US005955355A

United States Patent [19]
Chen et al.

[11] Patent Number: 5,955,355
[45] Date of Patent: Sep. 21, 1999

[54] CHROMOSOME 18 MARKER

[75] Inventors: Hong Chen, Brookline, Mass.; Nelson B. Freimer, San Francisco, Calif.

[73] Assignees: Millennium Pharmaceuticals, Inc., Cambridge, Mass.; The Regents University of California, Oakland, Calif.

[21] Appl. No.: 08/828,010

[22] Filed: Mar. 27, 1997

[51] Int. Cl.⁶ .................................................. C12N 15/00
[52] U.S. Cl. ...................... 435/320.1; 435/243; 435/325; 536/23.1; 536/23.5
[58] Field of Search ........................... 424/570; 435/69.1, 435/172.1, 320.1, 243, 325; 530/380, 827, 839; 536/23.1, 23.5, 24.34; 935/1, 6, 9, 18, 23, 33, 52, 70

[56] References Cited

U.S. PATENT DOCUMENTS

| | | |
|---|---|---|
| 4,109,496 | 8/1978 | Allemann et al. . |
| 4,215,051 | 7/1980 | Schroeder et al. . |
| 4,376,110 | 3/1983 | David et al. . |
| 4,683,202 | 7/1987 | Mullis . |
| 4,816,397 | 3/1989 | Boss et al. . |
| 4,816,567 | 3/1989 | Cabilly et al. . |
| 4,873,191 | 10/1989 | Wagner et al. . |
| 4,946,778 | 8/1990 | Ladner et al. . |
| 5,075,217 | 12/1991 | Weber . |
| 5,093,246 | 3/1992 | Cech et al. . |
| 5,364,759 | 11/1994 | Caskey et al. . |
| 5,399,346 | 3/1995 | Anderson et al. . |
| 5,585,089 | 12/1996 | Queen et al. . |

FOREIGN PATENT DOCUMENTS

| | | |
|---|---|---|
| WO 88/04300 | 6/1988 | WIPO . |
| WO 88/09810 | 12/1988 | WIPO . |
| WO 89/10134 | 11/1989 | WIPO . |
| WO 90/11364 | 10/1990 | WIPO . |

OTHER PUBLICATIONS

M. Baron, Genetic linkage and bipolar affective disorder: progress and pitfalls, Mol. Psych. 2:200–210, 1997.
H. Ewald et al., Susceptibility loci for bipolar affective disorder on chromosome 18?, Psych. Gen. 7:1–12, 1997.
D.F. MacKinnon et al., Genetics of Manic Depressive Illness, Annu. Rev. Neurosci. 20:355–73, 1997.
B. Lewin, Genes IV, p. 805, 1990.
Altschul, S. et al., 1990, "Basic Local Alignment Search Tool", J. Mol. Biol. 215:403–410.
Ausubel, F.M. et al., eds., 1989, Current Protocols in Molecular Biology, vol. I, Green Publishing Associates, Inc., and John Wiley & Sons, Inc., NY, at p. 2.10.3.
Babiychuk, E. et al., 1995, "*Arabidopsis thaliana* NADPH Oxidoreductase Homologs Confer Tolerance of Yeasts toward the Thiol–oxidizing Drug Diamide" J. of Biological Chemistry 270:26224–26231.
Baron, M. et al., 1993, "Diminished Support for Linkage Between Manic Depressive Illness and X–Chromosome Markers in Three Israeli Pedigrees", Nature Genetics 3:49–55.

Baron, M. et al., 1987, "Genetic Linkage Between X–Chromosome Markers and Bipolar Affective Illness", Nature 326:289–292.
Been and Cech, 1986, "One Binding Site Determines Sequence Specificity of Tetrahymena Pre–rRNA Self–Splicing, Trans–Splicing, and RNA Enzyme Activity", Cell 47:207–216.
Benoist and Chambon, 1981, "In Vivo Sequence Requirements of the SV40 Early Promoter Region", Nature 290:304–310.
Berrettini, W. et al., 1994, "Chromosome 18 DNA Markers and Manic–Depressive Illness: Evidence for a Susceptibility Gene", Proc. Natl. Acad. Sci. USA 91:5918–5921.
Bertelsen, A. et al., 1977, "A Danish Twin Study of Manic–Depressive Disorders", Brit. J. Psychiat. 130:330–351.
Bird, R. et al., 1988, "Single–Chain Antigen–Binding Proteins", Science 242:423–426.
Bitter, G. et al., 1987, "Expression and Secretion Vectors for Yeast", Methods in Enzymology 153:516–544.
Brinster, R. et al., 1982, "Regulation of Metallothionein–Thymidine Kinase Fusion Plasmids Injected into Mouse Eggs", Nature 296:39–42.
Butler, J.E., 1981, "The Amplified ELISA: Principles of and Applications for the Comparitive Quantitation of Class and Subclass Antibodies and the Distribution of Antibodies and Antigens in Biochemical Separates", Methods in Enzymology 73:482–523.
Campbell, K.H.S. et al., 1996, "Sheep Cloned by Nuclear Transfer from a Cultured Cell Line", Nature 380:64–66.
Chien, C. et al., 1991, "The Two–Hybrid System: A Method to Identify and Clone Genes for Proteins that Interact with a Protein of Interest", Proc. Natl. Acad. Sci. USA 88:9578–9582.

(List continued on next page.)

*Primary Examiner*—Paula K. Hutzell
*Assistant Examiner*—Susan Pellegrino
*Attorney, Agent, or Firm*—Pennie & Edmonds LLP

[57] ABSTRACT

The present invention relates to the mammalian fsh05 gene, a novel gene associated with bipolar affective disorder (BAD) in humans. The invention encompasses fsh05 nucleic acids, recombinant DNA molecules, cloned genes or degenerate variants thereof, fsh05 gene products and antibodies directed against such gene products, cloning vectors containing mammalian fsh05 gene molecules, and hosts that have been genetically engineered to express such molecules. The invention further relates to methods for the identification of compounds that modulate the expression of fsh05 and to using such compounds as therapeutic agents in the treatment of fsh05 disorders and neuropsychiatric disorders. The invention also relates to methods for the diagnostic evaluation, genetic testing and prognosis of fsh05 disorders and neuropsychiatric disorders including schizophrenia, attention deficit disorder, a schizoaffective disorder, a bipolar affective disorder or a unipolar affective disorder, and to methods and compositions for the treatment these disorders.

15 Claims, 4 Drawing Sheets

OTHER PUBLICATIONS

Cohen, D. et al., 1993, "Première Génération de la Carte Physique du Génome Humain", C.R. Acad. Sci. 316:1484–1488.

Colbère–Garapin, F. et al., 1981, "A New Dominant Hybrid Selective Market for Higher Eukaryotic Cells", J. Mol. Biol. 150:1–14.

Cole, S.P.C. et al., 1985, "The EBV–Hybridoma Technique and its Application to Human Lung Cancer", Monoclonal Antibodies and Cancer Therapy, pp. 77–96.

Cote, R. et al., 1983, "Generation of Human Monoclonal Antibodies Reactive with Cellular Antigens", Proc. Natl. Acad. Sci. USA 80:2026–2030.

Creighton, T., 1983, "Proteins: Structures and Molecular Principles", W.H. Freeman & Co., NY, pp. 34–49.

Dunn, K.J. et al., 1996, "Rapid Neurite Formation in a Human Cortical Neuronal Cell Line", Int. J. Devl. Neuroscience 14:61–68.

Egeland, J. et al., 1987, "Bipolar Affective Disorders Linked to DNA Markers on Chromosome 11", Nature 325:783–787.

Freimer, N. et al., 1996, "Genetic Mapping Using Haplotype, Association and Linkage Methods Suggests a Locus for Severe Bipolar Disorder (BPI) at 18q22–q23", Nature Genetics 12:436–441.

Freimer and Reus, 1992, in The Molecular and Genetic Basis of Neurological Disease, Rosenberg et al., eds., Butterworths, NY, pp. 951–965.

Freimer, N.B. et al., 1996, "An Approach to Investigating Linkage for Bipolar Disorder Using Large Costa Rican Pedigrees", Neuropsychiatric Genetics 67:254–263.

Gautier, C. et al., 1987, "α–DNA IV: α–Anomeric and β–Anomeric Tetrathymidylates Covalently Linked to Intercalating Oxazolopyridocarbazole. Synthesis, Physicochemical Properties and Poly (rA) Binding", Nucleic Acids Research 15:6625–6641.

Gordon, J., 1989, "Transgenic Animals", Intl. Rev. Cytol. 115:171–229.

Gu, H. et al., 1994, "Deletion of a DNA Polymerase β Gene Segment in T Cells Using Cell Type–Specific Gene Targeting", Science 265:103–106.

Haseloff and Gerlach, 1988, "Simple RNA Enzymes with New and Highly Specific Endoribonuclease Activities", Nature 334:585–591.

Helene, C. et al., 1992, "Control of Gene Expression by Triple Helix–Forming Oligonucleotides", Ann. NY Acad. Sci. 660:27–36.

Hélène, C., 1991, "The Anti–Gene Strategy: Control of Gene Expression by Triplex–Forming–Oligonucleotides", Anti–Cancer Drug Design 6:569–584.

Houghten, R. et al., 1991, "Generation and Use of Synthetic Peptide Combinatorial Libraries for Basic Research and Drug Descovery", Nature 354:84–86.

Huse, W. et al., 1989, "Generation of a Large Combinatorial Library of the Immunoglobulin Repertoire in Phage Lambda", Science 246:1275–1281.

Huston, J. et al., 1988, "Protein Engineering of Antibody Binding Sites: Recovery of Specific Activity in an Anti–Digoxin Single–Chain Fv Analogue Produced in *Escherichia Coli*", Proc. Natl. Acad. Sci. USA 85:5879–5883.

Inoue, H. et al., 1987, "Sequence–Dependent Hydrolysis of RNA Using Modified Oligonucleotide Splints and RNase H", FEBS Letters 215:327–330.

Inoue, H. et al., 1987, "Synthesis and Hybridization Studies on Two Complementary Nona(2'–O–Methyl)Ribonucleotides", Nucleic Acids Research 15:6131–6148.

Inouye and Inouye, 1985, "Up–Promoter Mutations in the Ipp gene of *Escherichia coli*", Nucleic Acids Res. 13:3101–3109.

Janknecht, R. et al., 1991, "Rapid and Efficient Purification of Native Histidine–Tagged Protein Expressed by Recombinant Vaccinia Virus", Proc. Natl. Acad. Sci. USA 88:8972–8976.

Kelsoe, J. et al., 1989, "Re–Evaluation of the Linkage Relationship Between Chromosome 11p Loci and the Gene for Bipolar Affective Disorder in the Old Order Amish" Nature 342:238–243.

Kozbor and Roder, 1983, "The Production of Monoclonal Antibodies from Human Lymphocytes", Immunology Today 4:72–79.

Köhler and Milstein, 1975, "Continuous Cultures of Fused Cells Secreting Antibody of Predefined Specificity", Nature 256:495–497.

Lakso, M. et al., 1992, "Targeted Oncogene Activation by Site–Specific Recombination in Transgenic Mice", Proc. Natl. Acad. Sci. USA 89:6232–6236.

Lam, K. et al., 1991, "A New Type of Synthetic Peptide Library for Identifying Ligand–Binding Activity", Nature 354:82–84.

Lavitrano, M. et al., 1989, "Sperm Cells as Vectors for Introducing Foreign DNA into Eggs: Genetic Transformation of Mice", Cell 57:717–723.

Lemaitre, M. et al., 1987, "Specific Antiviral Activity of Poly(L–lysine)–Conjugated Oligodeoxyribonucleotide Sequence Complementary To Vesicular Stomatitis Virus N Protein mRNA Initiation Site", Proc. Natl. Acad. Sci. USA 84:648–652.

Letsinger, R. et al., 1989, "Cholesterol–Conjugated Oligonucleotides: Synthesis, Properties, and Activity as Inhibitors of Replication of Human Immunodeficiency Virus in Cell Culture", Proc. Natl. Acad. Sci. USA 86:6553–6556.

Levinson and Levitt, 1987, "Schizoaffective Mania Reconsidered", Am. J. Psychiatry 144:415–425.

Liu and Chang, 1994, "Identification by Extrachromosomal Amplification and Overexpression of a ζ–Crystallin/NADPH–Oxidoreductase Homologue Constitutively Expressed in Leishmania spp." Molecular and Biochemical Parasitology 66:201–210.

Lo, C., 1983, "Transformation by Iontophoretic Microinjection of DNA: Multiple Integrations Without Tandem Insertions", Molecular and Cellular Biology 3:1803–1814.

Logan and Shenk, 1984, "Adenovirus Tripartite Leader Sequence Enhances Translation of mRNAs Late After Infection", Proc. Natl. Acad. Sci. USA 81:3655–3659.

Lowy, I. et al., 1980, "Isolation of Transforming DNA: Cloning the Hamster aprt Gene", Cell 22:817–823.

Maher, L.J., 1992, "DNA Triple–Helix Formation: An Approach to Artificial Gene Repressors?", BioEssays 14:807–815.

Maier, W. et al., 1995, "Linkage Analysis Between Pericentrometric Markers on Chromosome 18 and Bipolar Disorder: A Replication Test", Psychiatry Research 59:7–15.

McInnes and Freimer, 1995, "Mapping Genes for Psychiatric Disorders and Behavioral Traits,", Current Opinion in Genetics and Development 5:376–381.

Meyers, 1995, in Molecular Biology and Biotechnology: A Comprehensive Desk Reference, VCH Publishers, NY, Fig. 4, p. 833.

Morrison, S. et al., 1984, "Chimeric Human Antibody Molecules: Mouse Antigen–Binding Domains with Human Constant Region Domains", Proc. Natl. Acad. Sci. USA 81:6851–6855.

Mulligan and Berg, 1981, "Selection for Animal Cells that Express the *Escherichia Coli* Gene Coding for Xanthine–Guanine Phosphoribosyltransferase", Proc. Natl. Acad. Sci. USA 78:2072–2076.

Murray, J. et al., 1994, "A Comprehenesive Human Linkage Map with Centimorgan Density", Science 265:2049–2054.

Neuberger, M. et al., 1984, "Recombinant Antibodies Possessing Novel Effector Functions", Nature 312:604–608.

O'Hare et al., 1981, "Transformation of Mouse Fibroblasts to Methotrexate Resistance by a Recombinant Plasmid Expressing a Prokaryotic Dihydrofolate Reductase", Proc. Natl. Acad. Sci. USA 78:1527–1531.

Pauls, D. et al., 1995, "Linkage Analyses of Chromosome 18 Markers Do Not Identify a Major Susceptibility Locus for Bipolar Affective Disorder in the Old Order Amish", Am. J. Hum. Genet. 57:636–643.

Pauls, D. et al., 1992, "Risks of Affective Illness Among First–Degree Relatives of Bipolar I Old Order Amish", Arch. Gen. Psychiatry 49:703–708.

Platt, K. et al., 1994, "Independent Regulation of Adipose Tissue–Specificity and Obesity Response of the Adipsin Promoter in Transgenic Mice", The J. of Biol. Chemistry 269:28558–28562.

Rommens, J.M. et al., 1994, in Identification of Transcribed Sequences, Hochgeschwender and Gardiner, eds. Plenum Press, NY, pp. 65–79.

Ronnett, G.V. et al., 1994, "Human Cerebral Cortical Cell Lines from Patients with Unilateral Megalencephaly and Rasmussen's Encephalitis", Neuroscience 63:1081–1099.

Ronnett, G. et al., 1990, "Human Cortical Neuronal Cell Line: Establishment from a Patient with Unilateral Megalencephaly", Science 248:603–605.

Rosenthal, N. et al., 1980, "Toward the Validation of RDC Schizoaffective Disorder", Arch. Gen. Psychiatry 37:804–810.

Rossi, J., 1994, "Making Ribozymes Work in Cells", Current Biology 4:469–471.

Rüther and Müller–Hill, 1983, "Easy Identification of cDNA Clones", The EMBO Journal 2:1791–1794.

Santerre, R. et al., 1984, "Expression of Prokaryotic Genes for Hygromycin B and G418 Resistance as Dominant–Selection Markers in Mouse L Cells", Gene 30:147–156.

Sarin, P. et al., 1988, "Inhibition of Acquired Immunodeficiency Syndrome Virus by Oligodeoxynucleoside Methyphosphonates", Proc. Natl. Acad. Sci. USA 85:7448–7451.

Sarver, N. et al., 1990, "Ribozymes as Potential Anti–HIV–1 Therapeutic Agents", Science 247:1222–1225.

Smith, G. et al., 1983, "Molecular Engineering of the *Autographa californica* Nuclear Polyhedrosis Virus Genome: Deletion Mutations Within the Polyhedrin Gene", J. of Virology 46:584–593.

Smithies, O. et al., "Insertion of DNA Sequences into the Human Chromosomal β–Globin Locus by Homologous Recombination", Nature 317:230–234.

Songyang, Z. et al., 1993, "SH2 Domains Recognize Specific Phosphopeptide Sequences", Cell 72:767–778.

Stein, C.A. et al., 1988, "Physiochemical Properties of Phosphorothioate Oligodeoxynucleotides", Nucleic Acids Research 16:3209–3221.

Straub, R. et al., 1994, "A Possible Vulnerability Locus for Bipolar Affective Disorder on Chromosome 21q22.3", Nature Genetics 8:291–296.

Szybalska and Szybalski, 1962, "Genetics of Human Cell Lines, IV. DNA–Mediated Heritable Transformation of a Biochemical Trait", Proc. Natl. Acad. Sci. USA 48:2026–2034.

Takeda, S. et al., 1985, "Construction of Chimaeric Processed Immunoglobulin Genes Containing Mouse Variable and Human Constant Region Sequences", Nature 314:452–454.

Thomas and Capecchi, 1987, "Site–Directed Mutagenesis by Gene Targeting in Mouse Enbryo–Derived Stem Cells", Cell 51:503–512.

Thompson, S. et al., 1989, "Germ Line Transmission and Expression of a Corrected HPRT Gene Produced by Gene Targeting in Embryonic Stem Cells", Cell 56:313–321.

Van der Krol, A. et al., 1988, "Modulation of Eukaryotic Gene Expression by Complementary RNA or DNA Sequences", BioTechniques 6:958–976.

Van der Putten, H. et al., 1985, "Efficient Insertion of Genes into the Mouse Germ Line Via Retroviral Vectors", Proc. Natl. Acad. Sci. USA 82:6148–6152.

Van Heeke and Schuster, 1989, "Expression of Human Asparagine Synthetase in *Escherchia coli*", J. of Biological Chemistry 264:5503–5509.

Voller, A. et al., 1978, "Enzyme Immunoassays with Special Reference to ELISA Techniques,", J. of Clinical Pathology 31:507–520.

Wagner, M. et al., 1981, "Nucleotide Sequence of the Thymidine Kinase Gene of Herpes Simplex Virus Type 1", Proc. Natl. Acad. Sci. USA 78:1441–1445.

Ward, E.S. et al., 1989, "Binding Activities of a Repertoire of Single Immunoglobulin Variable Domains Secreted from *Escherichia coli*", Nature, 334:544–546.

Westlund, K.N. et al., 1992, "Effects of Nerve Growth Factor and Acetyl–L–Carnitine Arginyl Amide on the Human Neuronal Line HCN–1A", Int.J.Devl. Neuroscience 10:361–373.

Wigler, M. et al., 1980, "Transformation of Mammalian Cells with an Amplifiable Dominant–Acting Gene", Proc. Natl. Acad. Sci. USA 77:3567–3570.

Wigler, M. et al., 1977, "Transfer of Purified Herpes Virus Thymidine Kinase Gene to Cultured Mouse Cells", Cell 11:223–232.

Wilmut, I. et al., 1997, "Viable Offspring Derived from Fetal and Adult Mammalian Cells", Nature 385:810–813.

Yamamoto, T. et al., 1980, "Identification of a Functional Promoter in the Long Terminal Repeat of Rous Sarcoma Virus", Cell 22:787–797.

Zaug and Cech, 1986, "The Intervening Sequence RNA of Tetrahymena is an Enzyme", Science 231:470–475.

Zaug, A. et al., 1986, "The Tetrahymena Ribozyme Acts like an RNA Restriction Endonuclease", Nature 324:429–433.

Zaug, A. et al., 1984, "A Labile Phosphodiester Bond at the Ligation Junction in a Circular Intervening Sequence RNA", Science 224:574–578.

Zon, G. et al., 1988, "Oligonucleotide Analogues as Potential Chemotherapeutic Agents", Pharmaceutical Research 5:539–549.

```
D   I   N   Y   S   A   G   R   Y   D   P   S   V   K   P   P   F   D   I   G    20
GAC ATC AAC TAT TCA GCA GGC CGC TAT GAC CCC TCA GTT AAG CCT CCC TTT GAC ATA GGT   60

F   E   G   I   G   E   V   A   L   G   V   A   S   A   R   Y   T   T   V    40
TTC GAA GGC ATT GGG GAG GTG GCC CTA GGC GTG GCC AGT GCC AGA TAC ACA GTT          120

G   Q   A   V   A   Y   M   A   P   G   S   F   A   E   Y   T   V   V   P   A    60
GGC CAA GCT GTG GCT TAC ATG GCA CCT GGT TCT TTT GCT GAG TAC ACA GTG CCT GCC      180

S   I   A   T   P   V   P   S   V   K   P   E   Y   L   T   L   L   V   S   G    80
AGC ATT GCA ACT CCA GTG CCC TCA GTG AAA CCC GAG TAT CTT ACC CTG CTG GTA AGT GGC  240

T   T   A   Y   I   S   L   K   E   L   G   G   L   S   E   G   K   K   V   L   100
ACC ACC GCA TAC ATC AGC CTG AAA GAG CTC GGA GGA CTG TCG GAA GGG AAA AAA GTT TTG  300

V   T   A   A   G   T   G   Q   F   A   M   Q   L   S   K   A   F   L   K   K   120
GTG ACA GCA GCA GGT ACG GGC TTT GCC ATG CAG CTT TCA AAG GCA TTT CTG AAG AAG      360

C   H   V   I   G   T   C   S   S   D   E   R   K   A   F   L   K   S   L   G   140
TGC CAT GTA ATT GGA ACC TGC TCT TCT GAT GAA AGG AAA GCT TTT CTG AAA TCT CTT GGC  420

C   D   R   P   I   N   Y   K   T   E   P   V   G   T   V   L   K   Q   E   Y   160
TGT GAT CGT CCT ATC AAC TAT AAA ACT GAA CCC GTA GGT ACC GTC CTT AAG CAG GAG TAC  480

P   E   G   V   D   V   V   Y   E   S   V   G   G   A   M   F   D   L   A   V   180
CCT GAA GGT GTC GAT GTG GTC TAT GAA TCT GTT GGG GGA GCC ATG TTT GAC TTG GCT GTA  540
```

FIG.1A

```
  D   A   L   A   T   K   G   R   L   I   V   I   G   F   I   S   G   Y   Q   T   200
GAC GCC CTG GCT ACG AAA GGG CGC TTG ATA GTA ATA GGG TTT ATC TCT GGC TAC CAA ACT 600

P   T   G   L   S   P   V   K   A   G   T   L   P   A   K   L   L   K   K   S   220
CCT ACT GGC CTT TCG CCT GTG AAA GCA GGA ACA TTG CCA GCC AAA CTG CTC AAG AAA TCT 660

A   S   V   Q   G   F   F   L   N   H   Y   L   S   K   Y   Q   A   A   M   S   240
GCC AGC GTA CAG GGC TTC TTC CTG AAC CAT TAC CTT TCT AAG TAT CAA GCA GCC ATG AGC 720

H   L   L   E   M   C   V   S   G   D   L   V   C   E   V   D   L   G   D   L   260
CAC TTG CTC GAG ATG TGT GTG AGC GGA GAC CTG GTT TGT GAG GTG GAC CTT GGA GAT CTG 780

S   P   E   G   R   F   T   G   L   E   S   I   F   R   A   V   N   Y   M   Y   280
TCT CCA GAG GGC AGG TTT ACT GGC CTG GAG TCC ATA TTC CGT GCT GTC AAT TAT ATG TAC 840

M   G   K   N   T   G   K   I   V   E   L   P   H   S   V   N   S   K   L   300
ATG GGG AAA AAC ACT GGA AAA ATT GTA GTT GAA TTA CCT CAC TCT GTC AAC AGT AAG CTG 900
 *
TAA AAACAGAACAATGACATAATCAAGGGAGAAGAAAATGGGCACTTATGTCTCAGAA                     960
TTACTCAAATCAATTATTTATTTAGTTGGTAATGGATATATATTTCTTAAAACAAAAGTA                   1020
AGGTGTTAATGAATAGGTCTCTCCTTCCTCCTCCTCCTCCCTTGGGGAAGA                            1080
AAAAAAATGTGCTAATAAAACCTCGTGTCCAGATAGGTAAGAGGGAAAAACGCTTACATTCAAT               1140
TCTTTAGTCATGGATGGTCTCGTTCCAGATGTTATTGTTCCAGGGAACTAAATTCATTCC                   1200
TGATGCCAGATCTGATCGAGTCAGTAGTGTCTTCAGCTTGATCAGATTTTAAAATCAGTTT                  1260
TGAAAGTGGTTCCCGACTTCTTTGCTTTGGGAGAATTGGTCTTATGCTCATAAGCAGTT                    1320
CATGAGTGACAAGTGTAGCAAAAGCCAGCCATATATTTTCAGAATCTATATCCTCAGGAA                   1380
```

FIG.1B

```
ATGGTCCTTTTTTTCTATAAATCACCAACCAACTATCTAAATGGACATTTGGGGGAAT      1440
TCCCTCCCAAATTTGATTTGTTATTAGAAAAATGATTCCGTGAACACAGATGTGTTTTG     1500
AAGAAGTAGCACGTAATGGCTTTTATCTACCATCAACCTGATAAGGCACATGTGAAATGG    1560
AAATGTTCTCTTTCCTCTGAAGCAGCAAATTAATGTTGAAAACTTACATAGACAGAAAGT    1620
AGGTTTTGGAAAGGGAAACCACAGAGATTAGGGGGACTTAAAATTAATATATAGGCACAGGA  1680
AAGAGAAAAGTGTGCGCTCCATTCTCAGTGGGGGGTCACCACAAAACACGGGCCCAGGAGG   1740
GAAGCGCTGTCTAGGCACACGGCAAGGCCTTAGTAACAGCATGCTACACTGCTCGAGGTA    1800
CGGTATGTCCCATGCGCCCTGTGCACCGTAGAGACCTCAGTGCATCTCAAGGAAGAATACAT 1860
TTGCTTCTCCTTAGAGGCGTTCGAACTAGAAGCTATGCGTTACCTCTGATCTGGAAACAG   1920
AATAGCAGCCACTCATTCTGCATTCCCATTTTTCTCTCCACGTGTTCTGGTGGAATGAGA   1980
TGCTCCTTGGCACTATAGCCTGATGTCCCACATTGACCCACTGACCACACAGGAAAAGCA   2040
GCGAAACCTGCACCCTCTCTTCTGAGTCCAGCCTGGCTCATCGGCTTCCCTCTTAACC     2100
TTTAGTGCCCTGAAGACTGCTGCCGCTGTCACGTTGCGCTGAAACCCCATGGGCCCGTT    2160
CTGATTGAAGGTGAAGCCCACCAGATTATTTTCAAAGTCTTAGGTTTCGGTTCGGTATCTAA 2220
CCTGCTCAGTAAATATGGACGCAATTAAAGATGCTCTAGGAAAATTTGGGGACTGTATTA   2280
ATTTTCTTTCCTCCATCTGAGGAGCAGGAATCCTAATGTAGCTGCTAGCATGCACACAA    2340
ATTTTACAGATTTACTCATTTTCAGTGACCTAAGTGTGCTTCACTGATGTTATGGCTGCACTG 2400
TCAATTATATGGTAAATGGAACCAAATAAATGGCTTCACTGATGTTATGGCTGCACTG     2460
AAGGGAAATGTCACGGTAAATAGCTGCCAAATTATGGATCATGCCGAAGTGTCACAACTG   2520
CACTAAAGACAAATAGCGACTAGAGGCTATTGCCACTGTGACGCTTTGAGTTATGAAGA    2580
AGGGTAGCGGCCTGATGCGGAGGCTCTTTGTGTCCTCATTATAGCAAAGGGTTACTGGTGC  2640
AGGGGACTAGGAAAAACCCGTCCAGTGTGGTGCTTAGTTATTCATCCATCCCTTTCAGAC   2700
CTAACGAGCCACAGCCACACGGAAAGAGACTTTGCCTCACTTTTACATTCACAAACAAAC   2760
AAAGGAGGGGGAGCAGGTTTTATGAATGTAACTGTGCACAGGAAATGACTGGTAATGGA    2820
AAAATGTTGTAATAAATAATCTAATCAAGAATATATTAAATTAACATAGTCTATG        2880
TCCAAAAGGCTTAGTTGCTTCTTATGCAGATAAGGACATTACCAACTAAATGCTTCTTCGAA 2940
TTTCTCCCTTTGTAAAGACTTGGGAGTAAGCATTAACCAACTAAATGCTTCTTCGAA      3000
ACTGAAGTGAGTCCCGGGTTTGTTTCATTTTAATGGGAGGGTAATAAAGATGAAAGACCAA  3060
```

FIG. 1C

```
CATTTAACTGATGGATCCCCTTAAGCTACACAGAATAGAAATTTATTGTGTTTGAGGGAAT    3120
ATACTAAATGCAGCTATGTAAAAATAAAATTCAAACGCCCAGGATTAAAATAAAATATAA    3180
TCTGAAACCTCATGTCTCTCTTCCCCAAACTAAGAAAGTGCACTGCATGCTGTTTC        3240
ACTTATTCTAGAAAAACAGCATGAAAGATTCCTCCATTCAGATAATGCCAAAATATG       3300
TTAAACTTTTTTATTCTTTGAAAATGATTTGTAAATTGAGGGTCATAGTTCAGCA         3360
TCAGTTTCATCTTCTGGATTATTGTTCAAGACCAGCCTCTAATGGGAGGTGAAACGGTA     3420
CGATGGTCTCAACACCTTTCTTGTGAACTGTAATACATATCACAAAAGTACATCCATAA    3480
TTCAGGGCAATTGTCAGTCTTTTAGAGAAGGGGCCAGGGTGGAACAATCCCAGTGAGTA    3540
AATTATTTCTCAGCTTGCTTCTCTTGAGACTTCTCTGCATGTCGGGCTTAGGGTCACCAGCCGGGCAGGG    3600
TGGAAGGAGCTTGCTTCTCTTGAGAAACCAAGGAGTCCCAGTGATCTGTTACCATTGGTT   3660
ATGACTTCTAAAGAGAGCCAAATGCTATTCCTTCAAGCCTGTGTTTGCAGGCAGAAAATACCA 3720
GCAGTGTCATTTAGGGGTTCCTTTGATGATGACTACTGCTGTTAACTGACCTCAGCAAAA   3780
AAAAAAAAAAAA                                                    3794
```

FIG. 1D

CHROMOSOME 18 MARKER

This invention was supported in part by Grant Nos. R03 MH-48695, R01 MH-47563, R01-MH49499, and K21MH00916 from the National Institutes of Health. The U.S. Government may have rights in this invention.

1. INTRODUCTION

The present invention relates to the mammalian fsh05 gene, a novel gene associated with neuropsychiatric disorders in humans. The invention encompasses fsh05 nucleic acids, recombinant DNA molecules, cloned genes or degenerate variants thereof, fsh05 gene products and antibodies directed against such gene products, cloning vectors containing mammalian fsh05 gene molecules, and hosts that have been genetically engineered to express such molecules. The invention further relates to methods for the identification of compounds that modulate the expression, synthesis and activity of fsh05 and to using compounds such as those identified as therapeutic agents in the treatment of a fsh05 disorder or a neuropsychiatric disorder, including, by way of example and not of limitation, schizophrenia, attention deficit disorder, a schizoaffective disorder, a bipolar affective disorder or a unipolar affective disorder. The invention also relates to methods for the diagnostic evaluation, genetic testing and prognosis of a fsh05 disorder or of a neuropsychiatric disorder, including, by way of example and not of limitation, schizophrenia, attention deficit disorder, a schizoaffective disorder, a bipolar affective disorder or a unipolar affective disorder.

2. BACKGROUND OF THE INVENTION

There are only a few psychiatric disorders in which clinical manifestations of the disorder can be correlated with demonstrable defects in the structure and/or function of the nervous system. Well-known examples of such disorders include Huntington's disease, which can be traced to a mutation in a single gene and in which neurons in the striatum degenerate, and Parkinson's disease, in which dopaminergic neurons in the nigro-striatal pathway degenerate. The vast majority of psychiatric disorders, however, presumably involve subtle and/or undetectable changes, at the cellular and/or molecular levels, in nervous system structure and function. This lack of detectable neurological defects distinguishes "neuropsychiatric" disorders, such as schizophrenia, attention deficit disorders, schizoaffective disorder, bipolar affective disorders, or unipolar affective disorder, from neurological disorders, in which anatomical or biochemical pathologies are manifest. Hence, identification of the causative defects and the neuropathologies of neuropsychiatric disorders are needed in order to enable clinicians to evaluate and prescribe appropriate courses of treatment to cure or ameliorate the symptoms of these disorders.

One of the most prevalent and potentially devastating of neuropsychiatric disorders is bipolar affective disorder (BAD), also known as bipolar mood disorder (BP) or manic-depressive illness, which is characterized by episodes of elevated mood (mania) and depression (Goodwin, et al., 1990, *Manic Depressive Illness*, Oxford University Press, New York). The most severe and clinically distinctive forms of BAD are BP-I (severe bipolar affective (mood) disorder), which affects 2–3 million people in the United States, and SAD-M (schizoaffective disorder manic type). They are characterized by at least one full episode of mania, with or without episodes of major depression (defined by lowered mood, or depression, with associated disturbances in rhythmic behaviors such as sleeping, eating, and sexual activity). BP-I often co-segregates in families with more etiologically heterogeneous syndromes, such as with a unipolar affective disorder such as unipolar major depressive disorder (MDD), which is a more broadly defined phenotype (Freimer and Reus, 1992, in *The Molecular and Genetic Basis of Neurological Disease*, Rosenberg, et al., eds., Butterworths, New York, pp. 951–965; McInnes and Freimer, 1995, Curr. Opin. Genet. Develop., 5, 376–381). BP-I and SAD-M are severe mood disorders that are frequently difficult to distinguish from one another on a cross-sectional basis, follow similar clinical courses, and segregate together in family studies (Rosenthal, et al., 1980, Arch. General Psychiat. 37, 804–810; Levinson and Levitt, 1987, Am. J. Psychiat. 144, 415–426; Goodwin, et al., 1990, *Manic Depressive Illness*, Oxford University Press, New York). Hence, methods for distinguishing neuropsychiatric disorders such as these are needed in order to effectively diagnose and treat afflicted individuals.

Currently, individuals are typically evaluated for BAD using the criteria set forth in the most current version of the American Psychiatric Association's Diagnostic and Statistical Manual of Mental Disorders (DSM). While many drugs have been used to treat individuals diagnosed with BAD, including lithium salts, carbamazepine and valproic acid, none of the currently available drugs are adequate. For example, drug treatments are effective in only approximately 60–70% of individuals diagnosed with BP-I. Moreover, it is currently impossible to predict which drug treatments will be effective in, for example, particular BP-I affected individuals. Commonly, upon diagnosis, affected individuals are prescribed one drug after another until one is found to be effective. Early prescription of an effective drug treatment, therefore, is critical for several reasons, including the avoidance of extremely dangerous manic episodes and the risk of progressive deterioration if effective treatments are not found.

The existence of a genetic component for BAD is strongly supported by segregation analyses and twin studies (Bertelson, et al., 1977, Br. J. Psychiat. 130, 330–351; Freimer and Reus, 1992, in *The Molecular and Genetic Basis of Neurological Disease*, Rosenberg, et al., eds., Butterworths, New York, pp. 951–965; Pauls, et al., 1992, Arch. Gen. Psychiat. 49, 703–708). Efforts to identify the chromosomal location of genes that might be involved in BP-I, however, have yielded disappointing results in that reports of linkage between BP-I and markers on chromosomes X and 11 could not be independently replicated nor confirmed in the re-analyses of the original pedigrees, indicating that with BAD linkage studies, even extremely high lod scores at a single locus, can be false positives (Baron, et al., 1987, Nature 326, 289–292; Egeland, et al., 1987, Nature 325, 783–787; Kelsoe, et al., 1989, Nature 342, 238–243; Baron, et al., 1993, Nature Genet. 3, 49–55).

Recent investigations have suggested possible localization of BAD genes on chromosomes 18p and 21q, but in both cases the proposed candidate region is not well defined and no unequivocal support exists for either location (Berrettini, et al., 1994, Proc. Natl. Acad. Sci. USA 91, 5918–5921; Murray, et al., 1994, Science 265, 2049–2054; Pauls, et al., 1995, Am. J. Hum. Genet. 57, 636–643; Maier, et al., 1995, Psych. Res. 59, 7–15; Straub, et al., 1994, Nature Genet. 8, 291–296).

Mapping genes for common diseases believed to be caused by multiple genes, such as BAD, may be complicated by the typically imprecise definition of phenotypes, by etiologic heterogeneity, and by uncertainty about the mode of genetic transmission of the disease trait. With neuropsychiatric disorders there is even greater ambiguity in distinguishing individuals who likely carry an affected genotype from those who are genetically unaffected. For example, one can define an affected phenotype for BAD by including one or more of the broad grouping of diagnostic classifications that constitute the mood disorders: BP-I, SAD-M, MDD, and bipolar affective (mood) disorder with hypomania and major depression (BP-II).

Thus, one of the greatest difficulties facing psychiatric geneticists is uncertainty regarding the validity of phenotype designations, since clinical diagnoses are based solely on clinical observation and subjective reports. Also, with complex traits such as neuropsychiatric disorders, it is difficult to genetically map the trait-causing genes because: (1) neuropsychiatric disorder phenotypes do not exhibit classic Mendelian recessive or dominant inheritance patterns attributable to a single genetic locus, (2) there may be incomplete penetrance, i.e., individuals who inherit a predisposing allele may not manifest disease; (3) a phenocopy phenomenon may occur, i.e., individuals who do not inherit a predisposing allele may nevertheless develop disease due to environmental or random causes; (4) genetic heterogeneity may exist, in which case mutations in any one of several genes may result in identical phenotypes.

Despite these difficulties, however, identification of the chromosomal location, sequence and function of genes and gene products responsible for causing neuropsychiatric disorders such as bipolar affective disorders is of great importance for genetic counseling, diagnosis and treatment of individuals in affected families.

3. SUMMARY OF THE INVENTION

It is an object of the present invention to identify genetic bases for neuropsychiatric disorders, provide methods of treating and diagnosing neuropsychiatric disorders, and provide methods for identifying compounds for use as part of therapeutic and/or diagnostic methods.

In particular, the present invention relates, first, to the mammalian fsh05 gene, a novel gene associated with neuropsychiatric disorders in humans, e.g., schizophrenia, attention deficit disorders, schizoaffective disorders, bipolar affective disorders, and/or unipolar affective disorders, including fsh05 nucleic acids, recombinant DNA molecules, cloned genes or degenerate variants thereof.

The invention further relates to novel mammalian fsh05 gene products and to antibodies directed against such mammalian fsh05 gene products, or conserved variants or fragments thereof. fsh05 nucleic acid and amino acid sequences are provided herein. The invention also relates to vectors, including expression vectors, containing mammalian fsh05 gene molecules, and hosts that have been genetically engineered to express such fsh05 gene products.

The invention further relates to methods for the treatment of fsh05 or neuropsychiatric disorders, wherein such methods comprise administering compounds which modulate the expression of a mammalian fsh05 gene and/or the synthesis or activity of a mammalian fsh05 gene product so symptoms of the disorder are ameliorated.

The invention further relates to methods for the treatment of mammalian fsh05 or neuropsychiatric disorders resulting from fsh05 gene mutations, wherein such methods comprise supplying the mammal with a nucleic acid molecule encoding an unimpaired fsh05 gene product such that an unimpaired fsh05 gene product is expressed and symptoms of the disorder are ameliorated.

The invention further relates to methods for the treatment of mammalian fsh05 or neuropsychiatric disorders resulting from fsh05 gene mutations, wherein such methods comprise supplying the mammal with a cell comprising a nucleic acid molecule that encodes an unimpaired fsh05 gene product such that the cell expresses the unimpaired fsh05 gene product and symptoms of the disorder are ameliorated.

In addition, the present invention is directed to methods that utilize the fsh05 gene and/or gene product sequences for the diagnostic evaluation, genetic testing and prognosis of a fsh05 disorder or a neuropsychiatric disorder. For example, the invention relates to methods for diagnosing fsh05 or neuropsychiatric disorders, wherein such methods comprise measuring fsh05 gene expression in a patient sample, or detecting a fsh05 mutation in the genome of the mammal suspected of exhibiting such a disorder.

The invention still further relates to methods for identifying compounds capable of modulate the expression of the mammalian fsh05 gene and/or the synthesis or activity of the mammalian fsh05 gene products, wherein such methods comprise contacting a compound to a cell that expresses a fsh05 gene, measuring the level of fsh05 gene expression, gene product expression or gene product activity, and comparing this level to the level of fsh05 gene expression, gene product expression or gene product activity produced by the cell in the absence of the compound, such that if the level obtained in the presence of the compound differs from that obtained in its absence, a compound capable of modulating the expression of the mammalian fsh05 gene and/or the synthesis or activity of the mammalian fsh05 gene products has been identified. fsh05 gene and/or gene products can also be utilized as markers for mapping of the region of the long arm of human chromosome 18 spanned by chromosomal markers D18S1121 and DS18S380.

The neuropsychiatric disorders referred to herein can include, but are not limited to, schizophrenia; attention deficit disorder; a schizoaffective disorder; a bipolar affective disorder, e.g., severe bipolar affective (mood) disorder (BP-I), bipolar affective (mood) disorder with hypomania and major depression (BP-II); schizoaffective disorder manic type (SAD-M); or a unipolar affective disorder e.g., unipolar major depressive disorder (MDD).

The term "fsh05 disorder" as used herein refers to a disorder involving an aberrant level of fsh05 gene expression, gene product synthesis and/or gene product activity relative to levels found in normal, unaffected, unimpaired individuals, levels found in clinically normal individuals, and/or levels found in a population whose level represents a baseline, average fsh05 level.

3.1. DEFINITIONS

As used herein, the following terms shall have the abbreviations indicated.

BAC, bacterial artificial chromosomes

BAD, bipolar affective disorder(s)

BP, bipolar mood disorder

BP-I, severe bipolar affective (mood) disorder

BP-II, bipolar affective (mood) disorder with hypomania and major depression bp, base pair(s)

EST, expressed sequence tag lod, logarithm of odds

MDD, unipolar major depressive disorder

RT-PCR, reverse transcriptase PCR

SSCP, single-stranded conformational polymorphism

SAD-M, schizoaffective disorder manic type

STS, short tag sequence

YAC, yeast artificial chromosome

4. BRIEF DESCRIPTION OF THE FIGURES

FIGS. 1A–1D depicts fsh05 nucleotide (SEQ ID NO:1) and amino acid sequences (SEQ ID NO:2).

5. DETAILED DESCRIPTION OF THE INVENTION

Described herein is the identification of a novel mammalian fsh05 gene, which is associated with neuropsychiatric disorders such as human bipolar affective disorder (BAD). fsh05 gene and gene product sequences are described in the example presented below in Section 6. This invention is based, in part, on the genetic and physical mapping of the fsh05 gene to a specific, narrow portion of chromosome 18, also described in the Example presented below in Section 6.

5.1. THE fsh05 GENE

The fsh05 gene is a novel gene associated with neuropsychiatric disorders, including BAD. Nucleic acid sequences of the identified fsh05 gene are described herein. As used herein, "fsh05 gene" refers to:

(a) a nucleic acid molecule containing the DNA sequence shown in FIG. 1D (SEQ ID NO:1) or contained in the cDNA clones FSH5-1 (ATCC accession No. 98317) and/or FSH5-2 (ATCC accession No. 98318), as deposited with the American Type Culture Collection (ATCC);

(b) any DNA sequence that encodes a polypeptide containing: the amino acid sequence shown in FIGS. 1A–1D (SEQ ID NO:2), the amino acid sequence encoded by the cDNA clones FSH5-1 (ATCC 98317) and/or FSH5-2 (ATCC 98318);

(c) any DNA sequence that hybridizes to the complement of the DNA sequences that encode the amino acid sequence shown in FIGS. 1A–1D (SEQ ID NO:2), or contained in the cDNA clones FSH5-1 (ATCC 98317) and/or FSH5-2 (ATCC 98318), as deposited with the ATCC, under highly stringent conditions, e.g., hybridization to filter-bound DNA in 0.5 M $NaHPO_4$, 7% sodium dodecyl sulfate (SDS), 1 mM EDTA at 65° C., and washing in 0.1×SSC/0.1% SDS at 68° C. (Ausubel F. M. et al., eds., 1989, Current Protocols in Molecular Biology, Vol. I, Green Publishing Associates, Inc., and John Wiley & sons, Inc., New York, at p. 2.10.3); and/or (d) any DNA sequence that hybridizes to the complement of the DNA sequences that encode the amino acid sequence shown in FIGS. 1A–1D (SEQ ID NO:2) or contained in the cDNA clones FSH5-1 (ATCC 98317) and/or FSH5-2 (ATCC 98318), as deposited with the ATCC, under less stringent conditions, such as moderately stringent conditions, e.g., washing in 0.2×SSC/0.1% SDS at 42° C. (Ausubel et al., 1989, supra), and encodes a gene product functionally equivalent to a fsh05 gene product.

The term "functionally equivalent to a fsh05 gene product," as used herein, refers to a gene product that exhibits at least one of the biological activities of an endogenous, unimpaired fsh05 gene. In one embodiment, a functionally equivalent fsh05 gene product is one that, when present in an appropriate cell type, is capable of ameliorating, preventing or delaying the onset of one or more symptoms of a fsh05 disorder. In another embodiment, a functionally equivalent fsh05 gene product is one that, when present in an appropriate cell type, is capable of ameliorating, preventing or delaying the onset of one or more symptoms of a neuropsychiatric disorder. In yet another embodiment, a functionally equivalent fsh05 gene product is one that, when present in an appropriate cell type, is capable of ameliorating, preventing or delaying the onset of one or more symptoms of a BAD, such as, for example, severe bipolar affective (mood) disorder, bipolar affective (mood) disorder with hypomania and major depression, or schizoaffective disorder manic type.

fsh05 sequences can include, for example either genomic DNA (gDNA) or cDNA sequences. When referring to a nucleic acid which encodes a given amino acid sequence, therefore, it is to be understood that the nucleic acid need not only be a cDNA molecule, but can also, for example, refer to a gDNA sequence from which an mRNA species is transcribed that is processed to encode the given amino acid sequence.

As used herein, fsh05 gene may also refer to degenerate variants of DNA sequences (a) through (d).

The invention also includes nucleic acid molecules, preferably DNA molecules, that hybridize to, and are therefore the complements of, the DNA sequences (a) through (d), in the preceding paragraph. Such hybridization conditions may be highly stringent or less highly stringent, as described above. In instances wherein the nucleic acid molecules are deoxyoligonucleotides ("oligos"), highly stringent conditions may refer, e.g., to washing in 6×SSC/0.05% sodium pyrophosphate at 37° C. (for 14-base oligos), 48° C. (for 17-base oligos), 55° C. (for 20-base oligos), and 60° C. (for 23-base oligos). These nucleic acid molecules may encode or act as fsh05 gene antisense molecules, useful, for example, in fsh05 gene regulation (for and/or as antisense primers in amplification reactions of fsh05 gene nucleic acid sequences). With respect to fsh05 gene regulation, such techniques can be used to regulate, for example, a fsh05 disorder or a neuropsychiatric disorder, such as BAD. Further, such sequences may be used as part of ribozyme and/or triple helix sequences, also useful for fsh05 gene regulation. Still further, such molecules may be used as components of diagnostic methods whereby, for example, the presence of a particular fsh05 allele responsible for causing a fsh05 disorder or neuropsychiatric disorder such as BAD, e.g., manic-depression, may be detected.

The invention also encompasses:

(a) DNA vectors that contain any of the foregoing fsh05 coding sequences and/or their complements (i.e., antisense);

(b) DNA expression vectors that contain any of the foregoing fsh05 coding sequences operatively associated with a regulatory element that directs the expression of the coding sequences; and (c) genetically engineered host cells that contain any of the foregoing fsh05 coding sequences operatively associated with a regulatory element that directs the expression of the coding sequences in the host cell.

As used herein, regulatory elements include but are not limited to inducible and non-inducible promoters, enhancers, operators and other elements known to those skilled in the art that drive and regulate expression. Such regulatory elements include but are not limited to the cytomegalovirus hCMV immediate early gene, the early or late promoters of SV40 adenovirus, the lac system, the trp system, the TAC system, the TRC system, the major operator and promoter regions of phage A, the control regions of fd coat protein, the promoter for 3-phosphoglycerate kinase, the promoters of acid iphosphatase, and the promoters of the yeast α-mating factors.

The invention further includes fragments of any of the DNA sequences disclosed herein.

In one embodiment, the fsh05 gene sequences of the invention are mammalian gene sequences, with human sequences being preferred.

In another embodiment, the fsh05 gene sequences of the invention are gene sequences encoding fsh05 gene products containing polypeptide portions corresponding to (that is, polypeptide portions exhibiting amino acid sequence similiarity to) the amino acid sequence depicted in FIG. 1, wherein the corresponding portion exhibits greater than about 50% amino acid identity with the FIGS. 1A–1D sequence. In yet another embodiment, the fsh05 gene sequences of the invention are gene sequences encoding fsh05 gene products containing polypeptide portions corresponding to (that is, polypeptide portions exhibiting amino acid sequence similiarity to) the amino acid sequence depicted in FIGS. 1A–1D wherein the corresponding portion exhibits greater than about 50% amino acid identity with the FIGS. 1A–1D sequence, averaged across the fsh05 gene product's entire length.

In addition to the human fsh05 gene sequences disclosed in FIGS. 1A–1D, additional fsh05 gene sequences can be identified and readily isolated, without undue experimentation, by molecular biological techniques well known in the art, used in conjunction with the fsh05 sequences disclosed herein. For example, additional human fsh05 gene sequences at the same or at different genetic loci as those disclosed in FIGS. 1A–1D can be isolated readily. There can exist, for example, genes at other genetic or physical loci within the human genome that encode proteins that have extensive homology to one or more domains of the fsh05 gene product and that encode gene products functionally equivalent to a fsh05 gene product. Further, homologous fsh05 gene sequences present in other species can be identified and isolated readily.

With respect to identification and isolation of fsh05 gene sequences present at the same genetic or physical locus as those sequences disclosed in FIGS. 1A–1D, such sequences can, for example, be obtained readily by utilizing standard sequencing and bacterial artificial chromosome (BAC) technologies in connection with BAC54 (Identification Reference EpHS996, ATCC Accession No. 98363).

For example, sheared libraries can be made from BAC54. Fragments of a convenient size, e.g., in the size range of approximately 1 kb, are cloned into a standard plasmid, and sequenced. Further fsh05 sequences can then readily be identified by alignment of the BAC sequences with the fsh05 sequences depicted in FIGS. 1A–1D. Alternatively, BAC subclones containing additional fsh05 sequences can be identified by identifying those subclones which hybridize to probes derived from the fsh05 sequences depicted in FIGS. 1A–1D.

With respect to the cloning of a fsh05 gene homologue in human or other species (e.g., mouse), the isolated fsh05 gene sequences disclosed herein may be labeled and used to screen a cDNA library constructed from mRNA obtained from appropriate cells or tissues (e.g., brain tissues) derived from the organism (e.g., mouse) of interest. The hybridization conditions used should be of a lower stringency when the cDNA library is derived from an organism different from the type of organism from which the labeled sequence was derived.

Alternatively, the labeled fragment may be used to screen a genomic library derived from the organism of interest, again, using appropriately stringent conditions. Low stringency conditions are well known to those of skill in the art, and will vary predictably depending on the specific organisms from which the library and the labeled sequences are derived. For guidance regarding such conditions see, for example, Sambrook, et al., 1989, Molecular Cloning, A Laboratory Manual, Second Edition, Cold Spring Harbor Press, N.Y.; and Ausubel, et al., 1989, Current Protocols in Molecular Biology, Green Publishing Associates and Wiley Interscience, N.Y.

Further, a fsh05 gene homologue may be isolated from, for example, human nucleic acid, by performing PCR using two degenerate oligonucleotide primer pools designed on the basis of amino acid sequences within the fsh05 gene product disclosed herein. The template for the reaction may be cDNA obtained by reverse transcription of mRNA prepared from, for example, human or non-human cell lines or tissue known or suspected to express a fsh05 gene allele (such as human brain cell lines e.g., ATCC CRL-7605, ATCC CRL-7948, ATCC CRL-2060 PFSK-1, ATCC CRL-2176 SW 598, American Type Culture Collection, Rockville, Md.; cortical neuronal cell lines, e.g., Ronnett, et al., 1990, Science 248, 603–605; Ronnett, et al., 1994, Neuroscience 63, 1081–1099; and Dunn, et al., 1996, Int. J. Dev. Neurosci. 14, 61–68; neuronal line HCN-1A, Westlund et al., 1992, Int. J. Dev. Neurosci. 10, 361–373).

The PCR product may be subcloned and sequenced to ensure that the amplified sequences represent the sequences of a fsh05 gene nucleic acid sequence. The PCR fragment may then be used to isolate a full length cDNA clone by a variety of methods. For example, the amplified fragment may be labeled and used to screen a bacteriophage cDNA library.

Alternatively, the labeled fragment may be used to isolate genomic clones via the screening of a genomic library.

PCR technology may also be utilized to isolate full length cDNA sequences. For example, RNA may be isolated, following standard procedures, from an appropriate cellular or tissue source (i.e., one known, or suspected, to express the fsh05 gene, such as, for example, blood samples or brain tissue samples obtained through biopsy or post-mortem). A reverse transcription reaction may be performed on the RNA using an oligonucleotide primer specific for the most 5' end of the amplified fragment for the priming of first strand synthesis. The resulting RNA/DNA hybrid may then be "tailed" with guanines using a standard terminal transferase reaction, the hybrid may be digested with RNAase H, and second strand synthesis may then be primed with a poly-C primer. Thus, cDNA sequences upstream of the amplified fragment may easily be isolated. For a review of cloning strategies that may be used, see e.g., Sambrook et al., 1989, supra.

fsh05 gene sequences may additionally be used to isolate mutant fsh05 gene alleles. Such mutant alleles may be isolated from individuals either known or proposed to have a genotype that contributes to the symptoms of a fsh05 disorder, or a neuropsychiatric disorder such as BAD, for example, manic-depression. Mutant alleles and mutant allele products may then be utilized in the therapeutic and diagnostic systems described below. Additionally, such fsh05 gene sequences can be used to detect fsh05 gene regulatory (e.g., promoter) defects which can be associated with a fsh05 disorder, or a neuropsychiatric disorder such as BAD.

A cDNA of a mutant fsh05 gene may be isolated, for example, by using PCR, a technique that is well known to those of skill in the art. In this case, the first cDNA strand may be synthesized by hybridizing an oligo-dT oligonucleotide to mRNA isolated from tissue known or suspected to be expressed in an individual putatively carrying the mutant fsh05 allele, and by extending the new strand with reverse transcriptase. The second strand of the cDNA is then synthesized using an oligonucleotide that hybridizes specifically to the 5' end of the normal gene. Using these two primers, the product is then amplified via PCR, cloned into a suitable vector, and subjected to DNA sequence analysis through methods well known to those of skill in the art. By comparing the DNA sequence of the mutant fsh05 allele to that of the normal fsh05 allele, the mutation(s) responsible for the loss or alteration of function of the mutant fsh05 gene product can be ascertained.

Alternatively, a genomic library can be constructed using DNA obtained from an individual suspected of or known to carry a mutant fsh05 allele, or a cDNA library can be constructed using RNA from a tissue known, or suspected, to express a mutant fsh05 allele. An unimpaired fsh05 gene or any suitable fragment thereof may then be labeled and used as a probe to identify the corresponding mutant fsh05 allele in such libraries. Clones containing the mutant fsh05 gene sequences may then be purified and subjected to sequence analysis according to methods well known to those of skill in the art.

Additionally, an expression library can be constructed utilizing cDNA synthesized from, for example, RNA isolated from a tissue known, or suspected, to express a mutant fsh05 allele in an individual suspected of or known to carry such a mutant allele. In this manner, gene products made by the putatively mutant tissue may be expressed and screened using standard antibody screening techniques in conjunction with antibodies raised against the normal fsh05 gene product, as described, below, in Section 5.3. (For screening techniques, see, for example, Harlow and Lane, eds., 1988, "Antibodies: A Laboratory Manual", Cold Spring Harbor Press, Cold Spring Harbor.)

In cases where a fsh05 mutation results in an expressed gene product with altered function (e.g., as a result of a missense or a frameshift mutation), a polyclonal set of anti-fsh05 gene product antibodies are likely to cross-react with the mutant fsh05 gene product. Library clones detected via their reaction with such labeled antibodies can be purified and subjected to sequence analysis according to methods well known to those of skill in the art. fsh05 mutations can further be detected using PCR amplification techniques. Primers can routinely be designed to amplify overlapping regions of the whole fsh05 sequence including the promoter region. In one embodiment, primers are designed to cover the exon-intron boundaries such that, first, coding regions can be scanned for mutations. Genomic DNA isolated from lymphocytes of normal and affected individuals is used as PCR template. PCR products from normal and affected individuals are compared, either by single strand conformational polymorphism (SSCP) mutation detection techniques and/or by sequencing. The mutations responsible for the loss or alteration of function of the mutant fsh05 gene product can then be ascertained.

5.2. PROTEIN PRODUCTS OF THE fsh05 GENE fsh05 gene products, or peptide fragments thereof, can be prepared for a variety of uses. For example, such gene products, or peptide fragments thereof, can be used for the generation of antibodies, in diagnostic assays, or for the identification of other cellular or extracellular gene products involved in the regulation of a fsh05 disorder, or a neuropsychiatric disorder such as BAD.

The amino acid sequence depicted in FIGS. 1A–1D (SEQ ID NO:2) represents a fsh05 gene product. The fsh05 gene product, sometimes referred to herein as a "fsh05 protein", includes those gene products encoded by the fsh05 gene sequences described in Section 5.1, above.

In addition, fsh05 gene products may include proteins that represent functionally equivalent (see Section 5.1 for a definition) gene products. Such an equivalent fsh05 gene product may contain deletions, including internal deletions, additions, including additions yielding fusion proteins, or substitutions of amino acid residues within and/or adjacent to the the amino acid sequence encoded by the fsh05 gene sequences described, above, in Section 5.1, but that result in a "silent" change, in that the change produces a functionally equivalent fsh05 gene product. Amino acid substitutions may be made on the basis of similarity in polarity, charge, solubility, hydrophobicity, hydrophilicity, and/or the amphipathic nature of the residues involved. For example, nonpolar (hydrophobic) amino acids include alanine, leucine, isoleucine, valine, proline, phenylalanine, tryptophan, and methionine; polar neutral amino acids include glycine, serine, threonine, cysteine, tyrosine, asparagine, and glutamine; positively charged (basic) amino acids include arginine, lysine, and histidine; and negatively charged (acidic) amino acids include aspartic acid and glutamic acid.

Alternatively, where alteration of function is desired, deletion or non-conservative alterations can be engineered to produce altered fsh05 gene products. Such alterations can, for example, alter one or more of the biological functions of the fsh05 gene product. Further, such alterations can be selected so as to generate fsh05 gene products that are better suited for expression, scale up, etc. in the host cells chosen. For example, cysteine residues can be deleted or substituted with another amino acid residue in order to eliminate disulfide bridges.

The fsh05 gene products, peptide fragments thereof and fusion proteins thereof, may be produced by recombinant DNA technology using techniques well known in the art. Thus, methods for preparing the fsh05 gene polypeptides, peptides, fusion peptide and fusion polypeptides of the invention by expressing nucleic acid containing fsh05 gene sequences are described herein. Methods that are well known to those skilled in the art can be used to construct expression vectors containing fsh05 gene product coding sequences and appropriate transcriptional and translational control signals. These methods include, for example, in vitro recombinant DNA techniques, synthetic techniques, and in vivo genetic recombination. See, for example, the techniques described in Sambrook, et al., 1989, supra, and Ausubel, et al., 1989, supra. Alternatively, RNA capable of encoding fsh05 gene product sequences may be chemically synthesized using, for example, synthesizers. See, for example, the techniques described in "Oligonucleotide Synthesis", 1984, Gait, ed., IRL Press, Oxford.

A variety of host-expression vector systems may be utilized to express the fsh05 gene coding sequences of the invention. Such host-expression systems represent vehicles by which the coding sequences of interest may be produced and subsequently purified, but also represent cells that may, when transformed or transfected with the appropriate nucleotide coding sequences, exhibit the fsh05 gene product of the invention in situ. These include but are not limited to microorganisms such as bacteria (e.g., *E. coli, B. subtilis*) transformed with recombinant bacteriophage DNA, plasmid DNA or cosmid DNA expression vectors containing fsh05 gene product coding sequences; yeast (e.g., Saccharomyces, Pichia) transformed with recombinant yeast expression vectors containing the fsh05 gene product coding sequences; insect cell systems infected with recombinant virus expression vectors (e.g., baculovirus) containing the fsh05 gene product coding sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing fsh05 gene product coding sequences; or mammalian cell systems (e.g., COS, CHO, BHK, 293, 3T3) harboring recombinant expression constructs containing promoters derived from the genome of mammalian cells (e.g., metallothionein promoter) or from mammalian viruses (e.g., the adenovirus late promoter; the vaccinia virus 7.5K promoter).

In bacterial systems, a number of expression vectors may be advantageously selected depending upon the use intended for the fsh05 gene product being expressed. For example, when a large quantity of such a protein is to be produced, for the generation of pharmaceutical compositions of fsh05 protein or for raising antibodies to fsh05 protein, for example, vectors that direct the expression of high levels of fusion protein products that are readily purified may be desirable. Such vectors include, but are not limited, to the *E. coli* expression vector pUR278 (Ruther et al., 1983, EMBO J. 2, 1791), in which the fsh05 gene product coding sequence may be ligated individually into the vector in frame with the lac Z coding region so that a fusion protein is produced; pIN vectors (Inouye and Inouye, 1985, Nucleic Acids Res. 13, 3101–3109; Van Heeke and Schuster, 1989, J. Biol. Chem. 264, 5503–5509); and the like. PGEX vectors may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. The pGEX vectors are designed to include thrombin or factor Xa protease cleavage sites so that the cloned target gene product can be released from the GST moiety.

In an insect system, *Autographa californica*, nuclear polyhedrosis virus (AcNPV) is used as a vector to express foreign genes. The virus grows in *Spodoptera frugiperda* cells. The fsh05 gene coding sequence may be cloned individually into non-essential regions (for example the polyhedrin gene) of the virus and placed under control of an ACNPV promoter (for example the polyhedrin promoter). Successful insertion of fsh05 gene coding sequence will result in inactivation of the polyhedrin gene and production of non-occluded recombinant virus (i.e., virus lacking the proteinaceous coat coded for by the polyhedrin gene). These recombinant viruses are then used to infect *Spodoptera frugiperda* cells in which the inserted gene is expressed. (e.g., see Smith, et al., 1983, J. Virol. 46, 584; Smith, U.S. Pat. No. 4,215,051).

In mammalian host cells, a number of viral-based expression systems may be utilized. In cases where an adenovirus is used as an expression vector, the fsh05 gene coding sequence of interest may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing fsh05 gene product in infected hosts. (e.g., See Logan and Shenk, 1984, Proc. Natl. Acad. Sci. USA 81, 3655–3659). Specific initiation signals may also be required for efficient translation of inserted fsh05 gene product coding sequences. These signals include the ATG initiation codon and adjacent sequences. In cases where an entire fsh05 gene, including its own initiation codon and adjacent sequences, is inserted into the appropriate expression vector, no additional translational control signals may be needed. However, in cases where only a portion of the fsh05 gene coding sequence is inserted, exogenous translational control signals, including, perhaps, the ATG initiation codon, must be provided. Furthermore, the initiation codon must be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (see Bittner, et al., 1987, Methods in Enzymol. 153, 516–544).

In addition, a host cell strain may be chosen that modulates the expression of the inserted sequences, or modifies and processes the gene product in the specific fashion desired. Such modifications (e.g., glycosylation) and processing (e.g., cleavage) of protein products may be important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells that possess the cellular machinery for proper processing of the primary transcript, glycosylation, and phosphorylation of the gene product may be used. Such mammalian host cells include but are not limited to CHO, VERO, BHK, HeLa, COS, MDCK, 293, 3T3, and WI38.

For long-term, high-yield production of recombinant proteins, stable expression is preferred. For example, cell lines that stably express the fsh05 gene product may be engineered. Rather than using expression vectors that contain viral origins of replication, host cells can be transformed with DNA controlled by appropriate expression control elements (e.g., promoter, enhancer, sequences, transcription terminators, polyadenylation sites, etc.), and a selectable marker. Following the introduction of the foreign DNA, engineered cells may be allowed to grow for 1–2 days in an enriched media, and then are switched to a selective media. The selectable marker in the recombinant plasmid confers resistance to the selection and allows cells to stably integrate the plasmid into their chromosomes and grow to form foci that in turn can be cloned and expanded into cell lines. This method may advantageously be used to engineer cell lines that express the fsh05 gene product. Such engineered cell lines may be particularly useful in screening and evaluation of compounds that affect the endogenous activity of the fsh05 gene product.

A number of selection systems may be used, including but not limited to the herpes simplex virus thymidine kinase (Wigler, et al., 1977, Cell 11, 223), hypoxanthine-guanine phosphoribosyltransferase (Szybalska and Szybalski, 1962, Proc. Natl. Acad. Sci. USA 48, 2026), and adenine phosphoribosyltransferase (Lowy, et al., 1980, Cell 22, 817) genes can be employed in $tk^-$, $hgprt^-$ or $aprt^-$ cells, respectively. Also, antimetabolite resistance can be used as the basis of selection for the following genes: dhfr, which confers resistance to methotrexate (Wigler, et al., 1980, Natl. Acad. Sci. USA 77, 3567; O'Hare, et al., 1981, Proc. Natl. Acad. Sci. USA 78, 1527); gpt, which confers resistance to mycophenolic acid (Mulligan and Berg, 1981, Proc. Natl. Acad. Sci. USA 78, 2072); neo, which confers resistance to the aminoglycoside G-418 (Colberre-Garapin, et al., 1981, J.

Mol. Biol. 150, 1); and hygro, which confers resistance to hygromycin (Santerre, et al., 1984, Gene 30, 147).

Alternatively, any fusion protein may be readily purified by utilizing an antibody specific for the fusion protein being expressed. For example, a system described by Janknecht, et al. allows for the ready purification of non-denatured fusion proteins expressed in human cell lines (Janknecht, et al., 1991, Proc. Natl. Acad. Sci. USA 88, 8972–8976). In this system, the gene of interest is subcloned into a vaccinia recombination plasmid such that the gene's open reading frame is translationally fused to an amino-terminal tag consisting of six histidine residues. Extracts from cells infected with recombinant vaccinia virus are loaded onto $Ni^{2+}$ nitriloacetic acid-agarose columns and histidine-tagged proteins are selectively eluted with imidazole-containing buffers.

The fsh05 gene products can also be expressed in transgenic animals. Animals of any species, including, but not limited to, mice, rats, rabbits, guinea pigs, pigs, micro-pigs, goats, sheep, and non-human primates, e.g., baboons, monkeys, and chimpanzees may be used to generate fsh05 transgenic animals. The term "transgenic," as used herein, refers to animals expressing fsh05 gene sequences from a different species (e.g., mice expressing human fsh05 sequences), as well as animals that have been genetically engineered to overexpress endogenous (i.e., same species) fsh05 sequences or animals that have been genetically engineered to no longer express endogenous fsh05 gene sequences (i.e., "knock-out" animals), and their progeny.

Any technique known in the art may be used to introduce an fsh05 gene transgene into animals to produce the founder lines of transgenic animals. Such techniques include, but are not limited to pronuclear microinjection (Hoppe and Wagner, 1989, U.S. Pat. No. 4,873,191); retrovirus mediated gene transfer into germ lines (Van der Putten, et al., 1985, Proc. Natl. Acad. Sci., USA 82, 6148–6152); gene targeting in embryonic stem cells (Thompson, et al., 1989, Cell 56, 313–321); electroporation of embryos (Lo, 1983, Mol. Cell. Biol. 3, 1803–1814); and sperm-mediated gene transfer (Lavitrano et al., 1989, Cell 57, 717–723) (For a review of such techniques, see Gordon, 1989, Transgenic Animals, Intl. Rev. Cytol. 115; 171–229)

Any technique known in the art may be used to produce transgenic animal clones containing an fsh05 transgene, for example, nuclear transfer into enucleated oocytes of nuclei from cultured embryonic, fetal or adult cells induced to quiescence (Campbell, et al., 1996, Nature 380, 64–66; Wilmut, et al., Nature 385, 810–813).

The present invention provides for transgenic animals that carry an fsh05 transgene in all their cells, as well as animals that carry the transgene in some, but not all their cells, i.e., mosaic animals. The transgene may be integrated as a single transgene or in concatamers, e.g., head-to-head tandems or head-to-tail tandems. The transgene may also be selectively introduced into and activated in a particular cell type by following, for example, the teaching of Lasko et al. (Lasko, et al., 1992, Proc. Natl. Acad. Sci. USA 89, 6232–6236). The regulatory sequences required for such a cell-type specific activation will depend upon the particular cell type of interest, and will be apparent to those of skill in the art. When it is desired that the fsh05 gene transgene be integrated into the chromosomal site of the endogenous fsh05 gene, gene targeting is preferred. Briefly, when such a technique is to be utilized, vectors containing some nucleotide sequences homologous to the endogenous fsh05 gene are designed for the purpose of integrating, via homologous recombination with chromosomal sequences, into and disrupting the function of the nucleotide sequence of the endogenous fsh05 gene. The transgene may also be selectively introduced into a particular cell type, thus inactivating the endogenous fsh05 gene in only that cell type, by following, for example, the teaching of Gu, et al. (Gu, et al., 1994, Science 265, 103–106). The regulatory sequences required for such a cell-type specific inactivation will depend upon the particular cell type of interest, and will be apparent to those of skill in the art.

Once transgenic animals have been generated, the expression of the recombinant fsh05 gene may be assayed utilizing standard techniques. Initial screening may be accomplished by Southern blot analysis or PCR techniques to analyze animal tissues to assay whether integration of the transgene has taken place. The level of mRNA expression of the transgene in the tissues of the transgenic animals may also be assessed using techniques that include but are not limited to Northern blot analysis of tissue samples obtained from the animal, in situ hybridization analysis, and RT-PCR (reverse transcriptase PCR). Samples of fsh05 gene-expressing tissue, may also be evaluated immunocytochemically using antibodies specific for the fsh05 transgene product.

5.3. ANTIBODIES TO fsh05 GENE PRODUCTS

Described herein are methods for the production of antibodies capable of specifically recognizing one or more fsh05 gene product epitopes or epitopes of conserved variants or peptide fragments of the fsh05 gene products.

Such antibodies may include, but are not limited to, polyclonal antibodies, monoclonal antibodies (mAbs), humanized or chimeric antibodies, single chain antibodies, Fab fragments, F(ab')$_2$ fragments, fragments produced by a Fab expression library, anti-idiotypic (anti-Id) antibodies, and epitope-binding fragments of any of the above. Such antibodies may be used, for example, in the detection of a fsh05 gene product in an biological sample and may, therefore, be utilized as part of a diagnostic or prognostic technique whereby patients may be tested for abnormal levels of fsh05 gene products, and/or for the presence of abnormal forms of such gene products. Such antibodies may also be utilized in conjunction with, for example, compound screening schemes, as described, below, in Section 5.8, for the evaluation of the effect of test compounds on fsh05 gene product levels and/or activity. Additionally, such antibodies can be used in conjunction with the gene therapy techniques described, below, in Section 5.9.0.2 to, for example, evaluate the normal and/or engineered fsh05-expressing cells prior to their introduction into the patient.

Anti-fsh05 gene product antibodies may additionally be used as a method for the inhibition of abnormal fsh05 gene product activity. Thus, such antibodies may, therefore, be utilized as part of treatment methods for an fsh05 disorder or a neuropsychiatric disorder, such as BAD.

For the production of antibodies against a fsh05 gene product, various host animals may be immunized by injection with a fsh05 gene product, or a portion thereof. Such host animals may include, but are not limited to rabbits, mice, and rats, to name but a few. Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanin, dinitrophenol, and otentially useful human adjuvants such as BCG (bacille Calmette-Guerin) and *Corynebacterium parvum.*

Polyclonal antibodies are heterogeneous populations of antibody molecules derived from the sera of animals immunized with an antigen, such as a fsh05 gene product, or an antigenic functional derivative thereof. For the production of polyclonal antibodies, host animals such as those described above, may be immunized by injection with fsh05 gene product supplemented with adjuvants as also described above.

Monoclonal antibodies, which are homogeneous populations of antibodies to a particular antigen, may be obtained by any technique that provides for the production of antibody molecules by continuous cell lines in culture. These include, but are not limited to, the hybridoma technique of Kohler and Milstein, (1975, Nature 256, 495–497; and U.S. Pat. No. 4,376,110), the human B-cell hybridoma technique (Kosbor et al., 1983, Immunology Today 4, 72; Cole et al., 1983, Proc. Natl. Acad. Sci. USA 80, 2026–2030), and the EBV-hybridoma technique (Cole et al., 1985, Monoclonal Antibodies And Cancer Therapy, Alan R. Liss, Inc., pp. 77–96). Such antibodies may be of any immunoglobulin class including IgG, IgM, IgE, IgA, IgD and any subclass thereof. The hybridoma producing the mAb of this invention may be cultivated in vitro or in vivo. Production of high titers of mAbs in vivo makes this the presently preferred method of production.

In addition, techniques developed for the production of "chimeric antibodies" (Morrison, et al., 1984, Proc. Natl. Acad. Sci., 81, 6851–6855; Neuberger, et al., 1984, Nature 312, 604–608; Takeda, et al., 1985, Nature, 314, 452–454) by splicing the genes from a mouse antibody molecule of appropriate antigen specificity together with genes from a human antibody molecule of appropriate biological activity can be used. A chimeric antibody is a molecule in which different portions are derived from different animal species, such as those having a variable region derived from a murine mAb and a human immunoglobulin constant region. (See, e.g., Cabilly et al., U.S. Pat. No. 4,816,567; and Boss et al., U.S. Pat. No. 4,816397, which are incorporated herein by reference in their entirety.)

In addition, techniques have been developed for the production of humanized antibodies. (See, e.g., Queen, U.S. Pat. No. 5,585,089, which is incorporated herein by reference in its entirety.) An immunoglobuin light or heavy chain variable region consists of a "framework" region interrupted by three hypervariable regions, referred to as complementarity determining regions (CDRs). The extent of the framework region and CDRs have been precisely defined (see, "Sequences of Proteins of Immunological Interest", Kabat, E. et al., U.S. Department of Health and Human Services (1983). Briefly, humanized antibodies are antibody molecules from non-human species having one or more CDRs from the non-human species and a framework region from a human immunoglobulin molecule.

Alternatively, techniques described for the production of single chain antibodies (U.S. Pat. No. 4,946,778; Bird, 1988, Science 242, 423–426; Huston, et al., 1988, Proc. Natl. Acad. Sci. USA 85, 5879–5883; and Ward, et al., 1989, Nature 334, 544–546) can be adapted to produce single chain antibodies against fsh05 gene products. Single chain antibodies are formed by linking the heavy and light chain fragments of the Fv region via an amino acid bridge, resulting in a single chain polypeptide.

Antibody fragments that recognize specific epitopes may be generated by known techniques. For example, such fragments include but are not limited to: the $F(ab')_2$ fragments, which can be produced by pepsin digestion of the antibody molecule and the Fab fragments, which can be generated by reducing the disulfide bridges of the $F(ab')_2$ fragments. Alternatively, Fab expression libraries may be constructed (Huse, et al., 1989, Science, 246, 1275–1281) to allow rapid and easy identification of monoclonal Fab fragments with the desired specificity.

5.4. USES OF fsh05 GENE SEQUENCES, GENE PRODUCTS, AND ANTIBODIES

Described herein are various applications of fsh05 gene sequences, fsh05 gene products, including peptide fragments and fusion proteins thereof, and of antibodies directed against fsh05 gene products and peptide fragments thereof. Such applications include, for example, prognostic and diagnostic evaluation of a fsh05 disorder or a neuropsychiatric disorder, such as BAD, and the identification of subjects with a predisposition to such disorders, as described, below, in Section 5.5. Additionally, such applications include methods for the treatment of a fsh05 disorder or a neuropsychiatric disorder, such as BAD, as described, below, in Section 5.9, and for the identification of compounds that modulate the expression of the fsh05 gene and/or the synthesis or activity of the fsh05 gene product, as described below, in Section 5.8. Such compounds can include, for example, other cellular products that are involved in mood regulation and in fsh05 disorders and neuropsychiatric disorders, such as BAD. These compounds can be used, for example, in the amelioration of fsh05 disorders and neuropsychiatric disorders, such as BAD.

5.5. DIAGNOSIS OF ABNORMALITIES OF A fsh05 OR A NEUROPSYCHIATRIC DISORDER

A variety of methods can be employed for the diagnostic and prognostic evaluation of fsh05 disorders and neuropsychiatric disorders, such as BAD, and for the identification of subjects having a predisposition to such disorders.

Such methods may, for example, utilize reagents such as the fsh05 gene nucleotide sequences described in Sections 5.1, and antibodies directed against fsh05 gene products, including peptide fragments thereof, as described, above, in Section 5.3. Specifically, such reagents may be used, for example, for:

(1) the detection of the presence of fsh05 gene mutations, or the detection of either over- or under-expression of fsh05 gene mRNA relative to the state of a fsh05 disorder or a neuropsychiatric disorder, such as BAD;

(2) the detection of either an over- or an under-abundance of fsh05 gene product relative to the unaffected state; and (3) the detection of an aberrant level of fsh05 gene product activity relative to the unaffected state.

fsh05 gene nucleotide sequences can, for example, be used to diagnose an fsh05 or neuropsychiatric disorder using, for example, the techniques for fsh05 mutation detection described above in Section 5.1.

The methods described herein may be performed, for example, by utilizing pre-packaged diagnostic kits comprising at least one specific fsh05 gene nucleic acid or anti-fsh05 gene antibody reagent described herein, which may be conveniently used, e.g., in clinical settings, to diagnose patients exhibiting abnormalities of a fsh05 disorder or a neuropsychiatric disorder, such as BAD.

For the detection of fsh05 mutations, any nucleated cell can be used as a starting source for genomic nucleic acid. For the detection of fsh05 gene expression or fsh05 gene products, any cell type or tissue in which the fsh05 gene is expressed may be utilized.

Nucleic acid-based detection techniques are described, below, in Section 5.6. Peptide detection techniques are described, below, in Section 5.7.

5.6. DETECTION OF fsh05 NUCLEIC ACID MOLECULES

A variety of methods can be employed to screen for the presence of fsh05 mutations and to detect and/or assay levels of fsh05 nucleic acid sequences.

Mutations within the fsh05 gene can be detected by utilizing a number of techniques. Nucleic acid from any nucleated cell can be used as the starting point for such assay techniques, and may be isolated according to standard nucleic acid preparation procedures that are well known to those of skill in the art.

fsh05 nucleic acid sequences may be used in hybridization or amplification assays of biological samples to detect abnormalities involving fsh05 gene structure, including point mutations, insertions, deletions, inversions, translocations and chromosomal rearrangements. Such assays may include, but are not limited to, Southern analyses, single-stranded conformational polymorphism analyses (SSCP), and PCR analyses.

Diagnostic methods for the detection of fsh05 gene-specific mutations can involve for example, contacting and incubating nucleic acids including recombinant DNA molecules, cloned genes or degenerate variants thereof, obtained from a sample, e.g., derived from a patient sample or other appropriate cellular source, with one or more labeled nucleic acid reagents including recombinant DNA molecules, cloned genes or degenerate variants thereof, as described in Section 5.1, under conditions favorable for the specific annealing of these reagents to their complementary sequences within the fsh05 gene. Preferably, the lengths of these nucleic acid reagents are at least 15 to 30 nucleotides. After incubation, all non-annealed nucleic acids are removed from the nucleic acid:fsh05 molecule hybrid. The presence of nucleic acids that have hybridized, if any such molecules exist, is then detected. Using such a detection scheme, the nucleic acid from the cell type or tissue of interest can be immobilized, for example, to a solid support such as a membrane, or a plastic surface such as that on a microtiter plate or polystyrene beads. In this case, after incubation, non-annealed, labeled nucleic acid reagents of the type described in Section 5.1 are easily removed. Detection of the remaining, annealed, labeled fsh05 nucleic acid reagents is accomplished using standard techniques well-known to those in the art. The fsh05 gene sequences to which the nucleic acid reagents have annealed can be compared to the annealing pattern expected from a normal fsh05 gene sequence in order to determine whether a fsh05 gene mutation is present.

Alternative diagnostic methods for the detection of fsh05 gene specific nucleic acid molecules, in patient samples or other appropriate cell sources, may involve their amplification, e.g., by PCR (the experimental embodiment set forth in Mullis, 1987, U.S. Pat. No. 4,683,202), followed by the detection of the amplified molecules using techniques well known to those of skill in the art. The resulting amplified sequences can be compared to those that would be expected if the nucleic acid being amplified contained only normal copies of the fsh05 gene in order to determine whether a fsh05 gene mutation exists.

Additionally, well-known genotyping techniques can be performed to identify individuals carrying fsh05 gene mutations. Such techniques include, for example, the use of restriction fragment length polymorphisms (RFLPs), which involve sequence variations in one of the recognition sites for the specific restriction enzyme used.

Additionally, improved methods for analyzing DNA polymorphisms, which can be utilized for the identification of fsh05 gene mutations, have been described that capitalize on the presence of variable numbers of short, tandemly repeated DNA sequences between the restriction enzyme sites. For example, Weber (U.S. Pat. No. 5,075,217) describes a DNA marker based on length polymorphisms in blocks of (dC-dA)n-(dG-dT)n short tandem repeats. The average separation of (dC-dA)n-(dG-dT)n blocks is estimated to be 30,000–60,000 bp. Markers that are so closely spaced exhibit a high frequency co-inheritance, and are extremely useful in the identification of genetic mutations, such as, for example, mutations within the fsh05 gene, and the diagnosis of diseases and disorders related to fsh05 mutations.

Also, Caskey et al. (U.S. Pat. No. 5,364,759) describe a DNA profiling assay for detecting short tri and tetra nucleotide repeat sequences. The process includes extracting the DNA of interest, such as the fsh05 gene, amplifying the extracted DNA, and labelling the repeat sequences to form a genotypic map of the individual's DNA.

The level of fsh05 gene expression can also be assayed. For example, RNA from a cell type or tissue known, or suspected, to express the fsh05 gene, such as brain, may be isolated and tested utilizing hybridization or PCR techniques such as are described, above. The isolated cells can be derived from cell culture or from a patient. The analysis of cells taken from culture may be a necessary step in the assessment of cells to be used as part of a cell-based gene therapy technique or, alternatively, to test the effect of compounds on the expression of the fsh05 gene. Such analyses may reveal both quantitative and qualitative aspects of the expression pattern of the fsh05 gene, including activation or inactivation of fsh05 gene expression.

In one embodiment of such a detection scheme, a cDNA molecule is synthesized from an RNA molecule of interest (e.g., by reverse transcription of the RNA molecule into cDNA). A sequence within the cDNA is then used as the template for a nucleic acid amplification reaction, such as a PCR amplification reaction, or the like. The nucleic acid reagents used as synthesis initiation reagents (e.g., primers) in the reverse transcription and nucleic acid amplification steps of this method are chosen from among the fsh05 gene nucleic acid reagents described in Section 5.1. The preferred lengths of such nucleic acid reagents are at least 9–30 nucleotides. For detection of the amplified product, the nucleic acid amplification may be performed using radioactively or non-radioactively labeled nucleotides. Alternatively, enough amplified product may be made such that the product may be visualized by standard ethidium bromide staining or by utilizing any other suitable nucleic acid staining method.

Additionally, it is possible to perform such fsh05 gene expression assays "in situ", i.e., directly upon tissue sections (fixed and/or frozen) of patient tissue obtained from biopsies or resections, such that no nucleic acid purification is necessary. Nucleic acid reagents such as those described in Section 5.1 may be used as probes and/or primers for such in situ procedures (see, for example, Nuovo, G. J., 1992, "PCR In Situ Hybridization: Protocols And Applications", Raven Press, NY).

Alternatively, if a sufficient quantity of the appropriate cells can be obtained, standard Northern analysis can be performed to determine the level of mRNA expression of the fsh05 gene.

5.7. DETECTION OF fsh05 GENE PRODUCTS

Antibodies directed against unimpaired or mutant fsh05 gene products or conserved variants or peptide fragments thereof, which are discussed, above, in Section 5.3, may also be used as diagnostics and prognostics for a fsh05 disorder or a neuropsychiatric disorder, such as BAD, as described herein. Such methods may be used to detect abnormalities in the level of fsh05 gene product synthesis or expression, or abnormalities in the structure, temporal expression, and/or physical location of fsh05 gene product. The antibodies and immunoassay methods described below have, for example, important in vitro applications in assessing the efficacy of treatments for fsh05 disorders or neuropsychiatric disorders, such as BAD. Antibodies, or fragments of antibodies, such as those described below, may be used to screen potentially therapeutic compounds in vitro to determine their effects on fsh05 gene expression and fsh05 peptide production. The compounds that have beneficial effects on an fsh05 disorder or a neuropsychiatric disorder, such as BAD, can be identified, and a therapeutically effective dose determined.

In vitro immunoassays may also be used, for example, to assess the efficacy of cell-based gene therapy for an fsh05 disorder or a neuropsychiatric disorder, such as BAD. Antibodies directed against fsh05 peptides may be used in vitro to determine, for example, the level of fsh05 gene expression achieved in cells genetically engineered to produce fsh05 peptides. In the case of intracellular fsh05 gene products, such an assessment is done, preferably, using cell lysates or extracts. Such analysis will allow for a determination of the number of transformed cells necessary to achieve therapeutic efficacy in vivo, as well as optimization of the gene replacement protocol.

The tissue or cell type to be analyzed will generally include those that are known, or suspected, to express the fsh05 gene. The protein isolation methods employed herein may, for example, be such as those described in Harlow and Lane (1988, "Antibodies: A Laboratory Manual", Cold Spring Harbor Laboratory Press, Cold Spring Harbor, New York). The isolated cells can be derived from cell culture or from a patient. The analysis of cells taken from culture may be a necessary step in the assessment of cells to be used as part of a cell-based gene therapy technique or, alternatively, to test the effect of compounds on the expression of the fsh05 gene.

Preferred diagnostic methods for the detection of fsh05 gene products or conserved variants or peptide fragments thereof, may involve, for example, immunoassays wherein the fsh05 gene products or conserved variants or peptide fragments are detected by their interaction with an anti-fsh05 gene product-specific antibody.

For example, antibodies, or fragments of antibodies, such as those described, above, in Section 5.3, useful in the present invention may be used to quantitatively or qualitatively detect the presence of fsh05 gene products or conserved variants or peptide fragments thereof. This can be accomplished, for example, by immunofluorescence techniques employing a fluorescently labeled antibody (see below, this Section) coupled with light microscopic, flow cytometric, or fluorimetric detection. Such techniques are especially preferred for fsh05 gene products that are expressed on the cell surface.

The antibodies (or fragments thereof) useful in the present invention may, additionally, be employed histologically, as in immunofluorescence or immunoelectron microscopy, for in situ detection of fsh05 gene products or conserved variants or peptide fragments thereof. In situ detection may be accomplished by removing a histological specimen from a patient, and applying thereto a labeled antibody of the present invention. The antibody (or fragment) is preferably applied by overlaying the labeled antibody (or fragment) onto a biological sample. Through the use of such a procedure, it is possible to determine not only the presence of the fsh05 gene product, or conserved variants or peptide fragments, but also its distribution in the examined tissue. Using the present invention, those of ordinary skill will readily perceive that any of a wide variety of histological methods (such as staining procedures) can be modified in order to achieve such in situ detection.

Immunoassays for fsh05 gene products or conserved variants or peptide fragments thereof will typically comprise incubating a sample, such as a biological fluid, a tissue extract, freshly harvested cells, or lysates of cells, that have been incubated in cell culture, in the presence of a detectably labeled antibody capable of identifying fsh05 gene products or conserved variants or peptide fragments thereof, and detecting the bound antibody by any of a number of techniques well-known in the art.

The biological sample may be brought in contact with and immobilized onto a solid phase support or carrier such as nitrocellulose, or other solid support that is capable of immobilizing cells, cell particles or soluble proteins. The support may then be washed with suitable buffers followed by treatment with the detectably labeled fsh05 gene specific antibody. The solid phase support may then be washed with the buffer a second time to remove unbound antibody. The amount of bound label on solid support may then be detected by conventional means.

By "solid phase support or carrier" is intended any support capable of binding an antigen or an antibody. Well-known supports or carriers include glass, polystyrene, polypropylene, polyethylene, dextran, nylon, amylases, natural and modified celluloses, polyacrylamides, gabbros, and magnetite. The nature of the carrier can be either soluble to some extent or insoluble for the purposes of the present invention. The support material may have virtually any possible structural configuration so long as the coupled molecule is capable of binding to an antigen or antibody. Thus, the support configuration may be spherical, as in a bead, or cylindrical, as in the inside surface of a test tube, or the external surface of a rod. Alternatively, the surface may be flat such as a sheet, test strip, etc. Preferred supports include polystyrene beads. Those skilled in the art will know many other suitable carriers for binding antibody or antigen, or will be able to ascertain the same by use of routine experimentation.

The binding activity of a given lot of anti-fsh05 gene product antibody may be determined according to well known methods. Those skilled in the art will be able to determine operative and optimal assay conditions for each determination by employing routine experimentation.

One of the ways in which the fsh05 gene peptide-specific antibody can be detectably labeled is by linking the same to an enzyme and use in an enzyme immunoassay (EIA) (Voller, A., "The Enzyme Linked Immunosorbent Assay (ELISA)", 1978, Diagnostic Horizons 2, 1–7, Microbiological Associates Quarterly Publication, Walkersville, Md.); Voller, A. et al., 1978, J. Clin. Pathol. 31, 507–520; Butler, J. E., 1981, Meth. Enzymol. 73, 482–523; Maggio, E. (ed.), 1980, Enzyme Immunoassay, CRC Press, Boca Raton, Fla.,; Ishikawa, E. et al., (eds.), 1981, Enzyme Immunoassay, Kgaku Shoin, Tokyo). The enzyme which is bound to the antibody will react with an appropriate substrate, preferably a chromogenic substrate, in such a manner as to produce a chemical moiety that can be detected, for example, by spectrophotometric, fluorimetric or by visual means. Enzymes that can be used to detectably label the antibody include, but are not limited to, malate dehydrogenase, staphylococcal nuclease, delta-5-steroid isomerase, yeast alcohol dehydrogenase, α-glycerophosphate, dehydrogenase, triose phosphate isomerase, horseradish peroxidase, alkaline phosphatase, asparaginase, glucose oxidase, β-galactosidase, ribonuclease, urease, catalase, glucose-6-phosphate dehydrogenase, glucoamylase and acetylcholinesterase. The detection can be accomplished by colorimetric methods that employ a chromogenic substrate for the enzyme. Detection may also be accomplished by visual comparison of the extent of enzymatic reaction of a substrate in comparison with similarly prepared standards.

Detection may also be accomplished using any of a variety of other immunoassays. For example, by radioactively labeling the antibodies or antibody fragments, it is possible to detect fsh05 gene peptides through the use of a radioimmunoassay (RIA) (see, for example, Weintraub, B., Principles of Radioimmunoassays, Seventh Training Course on Radioligand Assay Techniques, The Endocrine Society, March, 1986). The radioactive isotope can be detected by such means as the use of a gamma counter or a scintillation counter or by autoradiography.

It is also possible to label the antibody with a fluorescent compound. When the fluorescently labeled antibody is exposed to light of the proper wave length, its presence can then be detected due to fluorescence. Among the most commonly used fluorescent labeling compounds are fluorescein isothiocyanate, rhodamine, phycoerythrin, phycocyanin, allophycocyanin, o-phthaldehyde and fluorescamine.

The antibody can also be detectably labeled using fluorescence emitting metals such as $^{152}$Eu, or others of the lanthanide series. These metals can be attached to the antibody using such metal chelating groups as diethylenetriaminepentacetic acid (DTPA) or ethylenediaminetetraacetic acid (EDTA).

The antibody also can be detectably labeled by coupling it to a chemiluminescent compound. The presence of the chemiluminescent-tagged antibody is then determined by detecting the presence of luminescence that arises during the course of a chemical reaction. Examples of particularly useful chemiluminescent labeling compounds are luminol, isoluminol, theromatic acridinium ester, imidazole, acridinium salt and oxalate ester.

Likewise, a bioluminescent compound may be used to label the antibody of the present invention. Bioluminescence is a type of chemiluminescence found in biological systems in which a catalytic protein increases the efficiency of the chemiluminescent reaction. The presence of a bioluminescent protein is determined by detecting the presence of luminescence. Important bioluminescent compounds for purposes of labeling are luciferin, luciferase And aequorin.

5.8. SCREENING ASSAYS FOR COMPOUNDS THAT MODULATE fsh05 GENE ACTIVITY

The following assays are designed to identify compounds that bind to a fsh05 gene product, intracellular proteins or portions of proteins that interact with a fsh05 gene product, compounds that interfere with the interaction of a fsh05 gene product with intracellular proteins and compounds that modulate the activity of fsh05 gene (i.e., modulate the level of fsh05 gene expression and/or modulate the level of fsh05 gene product activity). Assays may additionally be utilized that identify compounds that bind to fsh05 gene regulatory sequences (e.g., promoter sequences; see e.g., Platt, 1994, J. Biol. Chem. 269, 28558–28562), and that may modulate the level of fsh05 gene expression. Compounds may include, but are not limited to, small organic molecules, such as ones that are able to cross the blood-brain barrier, gain entry into an appropriate cell and affect expression of the fsh05 gene or some other gene involved in a fsh05 regulatory pathway, or intracellular proteins.

Methods for the identification of such intracellular proteins are described, below, in Section 5.8.2. Such intracellular proteins may be involved in the control and/or regulation of mood. Further, among these compounds are compounds that affect the level of fsh05 gene expression and/or fsh05 gene product activity and that can be used in the therapeutic treatment of fsh05 disorders or neuropsychiatric disorders such as BAD, as described, below, in Section 5.9.

Compounds may include, but are not limited to, peptides such as, for example, soluble peptides, including but not limited to, Ig-tailed fusion peptides, and members of random peptide libraries; (see, e.g., Lam, et al., 1991, Nature 354, 82–84; Houghten, et al., 1991, Nature 354, 84–86), and combinatorial chemistry-derived molecular library made of D- and/or L- configuration amino acids, phosphopeptides (including, but not limited to members of random or partially degenerate, directed phosphopeptide libraries; see, e.g., Songyang, et al., 1993, Cell 72, 767–778), antibodies (including, but not limited to, polyclonal, monoclonal, humanized, anti-idiotypic, chimeric or single chain antibodies, and FAb, F(ab')$_2$ and FAb expression library fragments, and epitope-binding fragments thereof), and small organic or inorganic molecules.

Such compounds may further comprise compounds, in particular drugs or members of classes or families of drugs, known to ameliorate or exacerbate the symptoms of a neuropsychiatric disorder such as BAD. Such compounds include antidepressants such as lithium salts, carbamazepine, valproic acid, lysergic acid diethylamide (LSD), p-chlorophenylalanine, p-propyldopacetamide dithiocarbamate derivatives e.g., FLA 63; anti-anxiety drugs, e.g., diazepam; monoamine oxidase (MAO) inhibitors, e.g., iproniazid, clorgyline, phenelzine and isocarboxazid; biogenic amine uptake blockers, e.g., tricyclic antidepressants such as desipramine, imipramine and amitriptyline; serotonin reuptake inhibitors e.g., fluoxetine; antipsychotic drugs such as phenothiazine derivatives (e.g., chlorpromazine (thorazine) and trifluopromazine)), butyrophenones (e.g., haloperidol (Haldol)), thioxanthene derivatives (e.g., chlorprothixene), and dibenzodiazepines (e.g., clozapine); benzodiazepines; dopaminergic agonists and antagonists e.g., L-DOPA, cocaine, amphetamine, α-methyl-tyrosine, reserpine, tetrabenazine, benzotropine, pargyline; noradrenergic agonists and antagonists e.g., clonidine, phenoxybenzamine, phentolamine, tropolone.

Compounds identified via assays such as those described herein may be useful, for example, in elaborating the biological function of the fsh05 gene product, and for ameliorating fsh05 disorders or neuropsychiatric disorders, such as BAD. Assays for testing the effectiveness of compounds, identified by, for example, techniques such as those described in Sections 5.8.1–5.8.3, are discussed, below, in Section 5.8.4.

5.8.1. IN VITRO SCREENING ASSAYS FOR COMPOUNDS THAT BIND TO THE fsh05 GENE PRODUCT In vitro systems may be designed to identify compounds capable of binding the fsh05 gene products of the invention.

Compounds identified may be useful, for example, in modulating the activity of unimpaired and/or mutant fsh05 gene products, may be useful in elaborating the biological function of the fsh05 gene product, may be utilized in screens for identifying compounds that disrupt normal fsh05 gene product interactions, or may in themselves disrupt such interactions.

The principle of the assays used to identify compounds that bind to the fsh05 gene product involves preparing a reaction mixture of the fsh05 gene product and the test compound under conditions and for a time sufficient to allow the two components to interact and bind, thus forming a complex that can be removed and/or detected in the reaction mixture. These assays can be conducted in a variety of ways. For example, one method to conduct such an assay would involve anchoring fsh05 gene product or the test substance onto a solid phase and detecting fsh05 gene product/test compound complexes anchored on the solid phase at the end of the reaction. In one embodiment of such a method, the fsh05 gene product may be anchored onto a solid surface, and the test compound, which is not anchored, may be labeled, either directly or indirectly.

In practice, microtiter plates may conveniently be utilized as the solid phase. The anchored component may be immobilized by non-covalent or covalent attachments. Non-covalent attachment may be accomplished by simply coating the solid surface with a solution of the protein and drying. Alternatively, an immobilized antibody, preferably a monoclonal antibody, specific for the protein to be immobilized may be used to anchor the protein to the solid surface. The surfaces may be prepared in advance and stored.

In order to conduct the assay, the non-immobilized component is added to the coated surface containing the anchored component. After the reaction is complete, unreacted components are removed (e.g., by washing) under conditions such that any complexes formed will remain immobilized on the solid surface. The detection of complexes anchored on the solid surface can be accomplished in a number of ways. Where the previously non-immobilized component is pre-labeled, the detection of label immobilized on the surface indicates that complexes were formed. Where the previously non-immobilized component is not pre-labeled, an indirect label can be used to detect complexes anchored on the surface; e.g., using a labeled antibody specific for the previously non-immobilized component (the antibody, in turn, may be directly labeled or indirectly labeled with a labeled anti-Ig antibody).

Alternatively, a reaction can be conducted in a liquid phase, the reaction products separated from unreacted components, and complexes detected; e.g., using an immobilized antibody specific for fsh05 gene product or the test compound to anchor any complexes formed in solution, and a labeled antibody specific for the other component of the possible complex to detect anchored complexes.

5.8.2. ASSAYS FOR INTRACELLULAR PROTEINS THAT INTERACT WITH fsh05 GENE PRODUCTS Any method suitable for detecting protein-protein interactions may be employed for identifying fsh05 protein-protein interactions.

Among the traditional methods that may be employed are co-immunoprecipitation, cross-linking and co-purification through gradients or chromatographic columns. Utilizing procedures such as these allows for the identification of proteins, including intracellular proteins, that interact with fsh05 gene products. Once isolated, such a protein can be identified and can be used in conjunction with standard techniques, to identify proteins it interacts with. For example, at least a portion of the amino acid sequence of a protein that interacts with the fsh05 gene product can be ascertained using techniques well known to those of skill in the art, such as via the Edman degradation technique (see, e.g., Creighton, 1983, "Proteins: Structures and Molecular Principles," W.H. Freeman & Co., N.Y., pp.34–49). The amino acid sequence obtained may be used as a guide for the generation of oligonucleotide mixtures that can be used to screen for gene sequences encoding such proteins. Screening made be accomplished, for example, by standard hybridization or PCR techniques. Techniques for the generation of oligonucleotide mixtures and the screening are well-known. (See, e.g., Ausubel, supra, and 1990, "PCR Protocols: A Guide to Methods and Applications," Innis, et al., eds. Academic Press, Inc., New York).

Additionally, methods may be employed that result in the simultaneous identification of genes that encode the a protein which interacts with an fsh05 protein. These methods include, for example, probing expression libraries with labeled fsh05 protein, using fsh05 protein in a manner similar to the well known technique of antibody probing of λgtll libraries.

One method that detects protein interactions in vivo, the two-hybrid system, is described in detail for illustration only and not by way of limitation. One version of this system has been described (Chien, et al., 1991, Proc. Natl. Acad. Sci. USA, 88, 9578–9582) and is commercially available from Clontech (Palo Alto, Calif.).

Briefly, utilizing such a system, plasmids are constructed that encode two hybrid proteins: one consists of the DNA-binding domain of a transcription activator protein fused to the fsh05 gene product and the other consists of the transcription activator protein's activation domain fused to an unknown protein that is encoded by a cDNA that has been recombined into this plasmid as part of a cDNA library. The DNA-binding domain fusion plasmid and the cDNA library are transformed into a strain of the yeast Saccharomyces cerevisiae that contains a reporter gene (e.g., HBS or lacZ) whose regulatory region contains the transcription activator's binding site. Either hybrid protein alone cannot activate transcription of the reporter gene: the DNA-binding domain hybrid cannot because it does not provide activation function and the activation domain hybrid cannot because it cannot localize to the activator's binding sites. Interaction of the two hybrid proteins reconstitutes the functional activator protein and results in expression of the reporter gene, which is detected by an assay for the reporter gene product.

The two-hybrid system or related methodology may be used to screen activation domain libraries for proteins that interact with the "bait" gene product. By way of example, and not by way of limitation, fsh05 gene products may be used as the bait gene product. Total genomic or cDNA sequences are fused to the DNA encoding an activation domain. This library and a plasmid encoding a hybrid of a bait fsh05 gene product fused to the DNA-binding domain are co-transformed into a yeast reporter strain, and the resulting transformants are screened for those that express the reporter gene. For example, and not by way of limitation, a bait fsh05 gene sequence, such as the open reading frame of the fsh05 gene, can be cloned into a vector such that it is translationally fused to the DNA encoding the DNA-binding domain of the GAL4 protein. These colonies are purified and the library plasmids responsible for reporter gene expression are isolated. DNA sequencing is then used to identify the proteins encoded by the library plasmids.

A cDNA library of the cell line from which proteins that interact with bait fsh05 gene product are to be detected can be made using methods routinely practiced in the art. According to the particular system described herein, for example, the cDNA fragments can be inserted into a vector such that they are translationally fused to the transcriptional activation domain of GAL4. This library can be co-transformed along with the bait fsh05 gene-GAL4 fusion plasmid into a yeast strain that contains a lacZ gene driven by a promoter that contains GAL4 activation sequence. A cDNA encoded protein, fused to GAL4 transcriptional activation domain, that interacts with bait fsh05 gene product will reconstitute an active GAL4 protein and thereby drive expression of the HIS3 gene. Colonies that express HIS3 can be detected by their growth on petri dishes containing semi-solid agar based media lacking histidine. The cDNA can then be purified from these strains, and used to produce and isolate the bait fsh05 gene-interacting protein using techniques routinely practiced in the art.

5.8.3. ASSAYS FOR COMPOUNDS THAT INTERFERE WITH fsh05 GENE PRODUCT MACROMOLECULE INTERACTION fsh05 gene products of the invention may, in vivo, interact with one or more macromolecules, including intracellular macromolecules, such as proteins. Such macromolecules may include, but are not limited to, nucleic acid molecules and those proteins identified via methods such as those described, above, in Sections 5.8.1–5.8.2. For purposes of this discussion, the macromolecules are referred to herein as "binding partners". Compounds that disrupt fsh05 binding in this way may be useful in regulating the activity of the fsh05 gene product, especially mutant fsh05 gene products. Such compounds may include, but are not limited to molecules such as peptides, and the like, as described, for example, in Section 5.8.2 above, which would be capable of gaining access to an fsh05 gene product.

The basic principle of the assay systems used to identify compounds that interfere with the interaction between the fsh05 gene product and its binding partner or partners involves preparing a reaction mixture containing the fsh05 gene product, and the binding partner under conditions and for a time sufficient to allow the two to interact and bind, thus forming a complex. In order to test a compound for inhibitory activity, the reaction mixture is prepared in the presence and absence of the test compound. The test compound may be initially included in the reaction mixture, or may be added at a time subsequent to the addition of fsh05 gene product and its binding partner. Control reaction mixtures are incubated without the test compound or with a placebo. The formation of any complexes between the fsh05 gene protein and the binding partner is then detected. The formation of a complex in the control reaction, but not in the reaction mixture containing the test compound, indicates that the compound interferes with the interaction of the fsh05 gene protein and the interactive binding partner. Additionally, complex formation within reaction mixtures containing the test compound and normal fsh05 gene protein may also be compared to complex formation within reaction mixtures containing the test compound and a mutant fsh05 gene protein. This comparison may be important in those cases wherein it is desirable to identify compounds that disrupt interactions of mutant but not normal fsh05 gene proteins.

The assay for compounds that interfere with the interaction of the fsh05 gene products and binding partners can be conducted in a heterogeneous or homogeneous format. Heterogeneous assays involve anchoring either the fsh05 gene product or the binding partner onto a solid phase and detecting complexes anchored on the solid phase at the end of the reaction. In homogeneous assays, the entire reaction is carried out in a liquid phase. In either approach, the order of addition of reactants can be varied to obtain different information about the compounds being tested. For example, test compounds that interfere with the interaction between the fsh05 gene products and the binding partners, e.g., by competition, can be identified by conducting the reaction in the presence of the test substance; i.e., by adding the test substance to the reaction mixture prior to or simultaneously with the fsh05 gene protein and interactive intracellular binding partner. Alternatively, test compounds that disrupt preformed complexes, e.g., compounds with higher binding constants that displace one of the components from the complex, can be tested by adding the test compound to the reaction mixture after complexes have been formed. The various formats are described briefly below.

In a heterogeneous assay system, either the fsh05 gene product or the interactive binding partner, is anchored onto a solid surface, while the non-anchored species is labeled, either directly or indirectly. In practice, microtiter plates are conveniently utilized. The anchored species may be immobilized by non-covalent or covalent attachments. Non-covalent attachment may be accomplished simply by coating the solid surface with a solution of the fsh05 gene product or binding partner and drying. Alternatively, an immobilized antibody specific for the species to be anchored may be used to anchor the species to the solid surface. The surfaces may be prepared in advance and stored.

In order to conduct the assay, the partner of the immobilized species is exposed to the coated surface with or without the test compound. After the reaction is complete, unreacted components are removed (e.g., by washing) and any complexes formed will remain immobilized on the solid surface. The detection of complexes anchored on the solid surface can be accomplished in a number of ways. Where the non-immobilized species is pre-labeled, the detection of label immobilized on the surface indicates that complexes were formed. Where the non-immobilized species is not pre-labeled, an indirect label can be used to detect complexes anchored on the surface; e.g., using a labeled antibody specific for the initially non-immobilized species (the antibody, in turn, may be directly labeled or indirectly labeled with a labeled anti-Ig antibody). Depending upon the order of addition of reaction components, test compounds that inhibit complex formation or that disrupt preformed complexes can be detected.

Alternatively, the reaction can be conducted in a liquid phase in the presence or absence of the test compound, the reaction products separated from unreacted components, and complexes detected; e.g., using an immobilized antibody specific for one of the binding components to anchor any complexes formed in solution, and a labeled antibody specific for the other partner to detect anchored complexes. Again, depending upon the order of addition of reactants to the liquid phase, test compounds that inhibit complex or that disrupt preformed complexes can be identified.

In an alternate embodiment of the invention, a homogeneous assay can be used. In this approach, a preformed complex of the fsh05 gene protein and the interactive binding partner is prepared in which either the fsh05 gene product or its binding partners is labeled, but the signal generated by the label is quenched due to complex formation (see, e.g., U.S. Pat. No. 4,109,496 by Rubenstein which utilizes this approach for immunoassays). The addition of a test substance that competes with and displaces one of the species from the preformed complex will result in the generation of a signal above background. In this way, test substances that disrupt fsh05 gene protein/binding partner interaction can be identified.

In a particular embodiment, the fsh05 gene product can be prepared for immobilization using recombinant DNA techniques described in Section 5.2. above. For example, the fsh05 coding region can be fused to a glutathione-S-transferase (GST) gene using a fusion vector, such as pGEX-5X-1, in such a manner that its binding activity is maintained in the resulting fusion protein. The interactive binding partner can be purified and used to raise a monoclonal antibody, using methods routinely practiced in the art and described above, in Section 5.3. This antibody can be labeled with the radioactive isotope $^{125}I$, for example, by methods routinely practiced in the art. In a heterogeneous assay, e.g., the GST-fsh05 fusion protein can be anchored to glutathione-agarose beads. The interactive binding partner can then be added in the presence or absence of the test compound in a manner that allows interaction and binding to occur. At the end of the reaction period, unbound material can be washed away, and the labeled monoclonal antibody can be added to the system and allowed to bind to the complexed components. The interaction between the fsh05 gene protein and the interactive binding partner can be detected by measuring the amount of radioactivity that remains associated with the glutathione-agarose beads. A successful inhibition of the interaction by the test compound will result in a decrease in measured radioactivity.

Alternatively, the GST-fsh05 gene fusion protein and the interactive binding partner can be mixed together in liquid in the absence of the solid glutathione-agarose beads. The test compound can be added either during or after the species are allowed to interact. This mixture can then be added to the glutathione-agarose beads and unbound material is washed away. Again the extent of inhibition of the fsh05 gene product/binding partner interaction can be detected by adding the labeled antibody and measuring the radioactivity associated with the beads.

In another embodiment of the invention, these same techniques can be employed using peptide fragments that correspond to the binding domains of the fsh05 protein and/or the interactive or binding partner (in cases where the binding partner is a protein), in place of one or both of the full length proteins. Any number of methods routinely practiced in the art can be used to identify and isolate the binding sites. These methods include, but are not limited to, mutagenesis of the gene encoding one of the proteins and screening for disruption of binding in a co-immunoprecipitation assay. Compensating mutations in the gene encoding the second species in the complex can then be selected. Sequence analysis of the genes encoding the respective proteins will reveal the mutations that correspond to the region of the protein involved in interactive binding. Alternatively, one protein can be anchored to a solid surface using methods described in this Section above, and allowed to interact with and bind to its labeled binding partner, which has been treated with a proteolytic enzyme, such as trypsin. After washing, a short, labeled peptide comprising the binding domain may remain associated with the solid material, which can be isolated and identified by amino acid sequencing. Also, once the gene coding for the segments can be engineered to express peptide fragments of the protein, which can then be tested for binding activity and purified or synthesized.

For example, and not by way of limitation, a fsh05 gene product can be anchored to a solid material as described, above, in this Section by making a GST-fsh05 fusion protein and allowing it to bind to glutathione agarose beads. The interactive binding partner obtained can be labeled with a radioactive isotope, such as $^{35}S$, and cleaved with a proteolytic enzyme such as trypsin. Cleavage products can then be added to the anchored GST-fsh05 fusion protein and allowed to bind. After washing away unbound peptides, labeled bound material, representing the binding partner binding domain, can be eluted, purified, and analyzed for amino acid sequence by well-known methods. Peptides so identified can be produced synthetically or fused to appropriate facilitative proteins using recombinant DNA technology.

5.8.4. ASSAYS FOR IDENTIFICATION OF COMPOUNDS THAT AMELIORATE A fsh05 DISORDER OR A NEUROPSYCHIATRIC DISORDER Compounds, including but not limited to binding compounds identified via assay techniques such as those described, above, in Sections 5.8.1–5.8.4, can be tested for the ability to ameliorate symptoms of a fsh05 disorder or a disorder of thought and/or mood, including thought disorders such as schizophrenia, schizotypal personality disorder; psychosis; mood disorders, such as schizoaffective disorders (e.g., schizoaffective disorder manic type (SAD-M); bipolar affective (mood) disorders, such as severe bipolar affective (mood) disorder (BP-I), bipolar affective (mood) disorder with hypomania and major depression (BP-II); unipolar affective disorders, such as unipolar major depressive disorder (MDD), dysthymic disorder; obsessive-compulsive disorders; phobias, e.g., agoraphobia; panic disorders; generalized anxiety disorders; somatization disorders and hypochondriasis; and attention deficit disorders. It should be noted that the assays described herein can identify compounds that affect fsh05 gene activity by either affecting fsh05 gene expression or by affecting the level of fsh05 gene product activity. For example, compounds may be identified that are involved in another step in the pathway in which the fsh05 gene and/or fsh05 gene product is involved and, by affecting this same pathway may modulate the effect of fsh05 on the development of a neuropsychiatric disorder such as BAD. Such compounds can be used as part of a therapeutic method for the treatment of the disorder.

Described below are cell-based and animal model-based assays for the identification of compounds exhibiting such an ability to ameliorate symptoms of a fsh05 disorder or a neuropsychiatric disorder, such as BAD.

First, cell-based systems can be used to identify compounds that may act to ameliorate symptoms of a fsh05 disorder or a neuropsychiatric disorder, such as BAD. Such cell systems can include, for example, recombinant or non-recombinant cell, such as cell lines, that express the fsh05 gene.

In utilizing such cell systems, cells that express fsh05 may be exposed to a compound suspected of exhibiting an ability to ameliorate symptoms of a fsh05 disorder or a neuropsychiatric disorder, such as BAD, at a sufficient concentration and for a sufficient time to elicit such an amelioration of such symptoms in the exposed cells. After exposure, the cells can be assayed to measure alterations in the expression of the fsh05 gene, e.g., by assaying cell lysates for fsh05 mRNA transcripts (e.g., by Northern analysis) or for fsh05 gene products expressed by the cell; compounds that modulate expression of the fsh05 gene are good candidates as therapeutics. Alternatively, the cells are examined to determine whether one or more cellular phenotypes associated with an fsh05 disorder or a neuropsychiatric disorder, such as BAD, has been altered to resemble a more normal or unimpaired, unaffected phenotype, or a phenotype more likely to produce a lower incidence or severity of disorder symptoms.

In addition, animal-based systems or models for a fsh05 disorder or a neuropsychiatric disorder, such as BAD, which may include, for example, fsh05 mice, may be used to identify compounds capable of ameliorating symptoms of the disorder. Such animal models may be used as test substrates for the identification of drugs, pharmaceuticals, therapies and interventions that may be effective in treating such disorders. For example, animal models may be exposed to a compound suspected of exhibiting an ability to ameliorate symptoms, at a sufficient concentration and for a sufficient time to elicit such an amelioration of symptoms of a fsh05 disorder or a neuropsychiatric disorder, such as BAD, in the exposed animals. The response of the animals to the exposure may be monitored by assessing the reversal of such symptoms.

With regard to intervention, any treatments that reverse any aspect of symptoms of a fsh05 disorder or a neuropsychiatric disorder, such as BAD, should be considered as candidates for human therapeutic intervention in such a disorder. Dosages of test agents may be determined by deriving dose-response curves, as discussed in Section 5.10.1, below.

5.9. COMPOUNDS AND METHODS FOR THE TREATMENT OF fsh05 DISORDERS OR NEUROPSYCHIATRIC DISORDERS Described below are methods and compositions whereby a fsh05 disorder or a disorder of thought and/or mood, such as BAD, may be treated.

For example, such methods can comprise administering compounds which modulate the expression of a mammalian fsh05 gene and/or the synthesis or activity of a mammalian fsh05 gene product so symptoms of the disorder are ameliorated.

Alternatively, in those instances whereby the mammalian fsh05 or neuropsychiatric disorders result from fsh05 gene mutations, such methods can comprise supplying the mammal with a nucleic acid molecule encoding an unimpaired fsh05 gene product such that an unimpaired fsh05 gene product is expressed and symptoms of the disorder are ameliorated.

In another embodiment of methods for the treatment of mammalian fsh05 or neuropsychiatric disorders resulting from fsh05 gene mutations, such methods can comprise supplying the mammal with a cell comprising a nucleic acid molecule that encodes an unimpaired fsh05 gene product such that the cell expresses the unimpaired fsh05 gene product and symptoms of the disorder are ameliorated.

In cases in which a loss of normal fsh05 gene product function results in the development of a fsh05 disorder or neuropsychiatric disorder phenotype, an increase in fsh05 gene product activity would facilitate progress towards an asymptomatic state in individuals exhibiting a deficient level of fsh05 gene expression and/or fsh05 gene product activity. Methods for enhancing the expression or synthesis of fsh05 can include, for example, methods such as those described below, in Section 5.9.2.

Alternatively, symptoms of fsh05 disorders or neuropsychiatric disorders, such as BAD, may be ameliorated by administering a compound that decreases the level of fsh05 gene expression and/or fsh05 gene product activity. Methods for inhibiting or reducing the level of fsh05 synthesis or expression can include, for example, methods such as those described in Section 5.9.1.

In one embodiment of treatment methods, the compounds administered do not comprise compounds, in particular drugs, reported to ameliorate or exacerbate the symptoms of a neuropsychiatric disorder, such as BAD. Such compounds include antidepressants such as lithium salts, carbamazepine, valproic acid, lysergic acid diethylamide (LSD), p-chlorophenylalanine, p-propyldopacetamide dithiocarbamate derivatives e.g., FLA 63; anti-anxiety drugs, e.g., diazepam; monoamine oxidase (MAO) inhibitors, e.g., iproniazid, clorgyline, phenelzine and isocarboxazid; biogenic amine uptake blockers, e.g., tricyclic antidepressants such as desipramine, imipramine and amitriptyline; serotonin reuptake inhibitors e.g., fluoxetine; antipsychotic drugs such as phenothiazine derivatives (e.g., chlorpromazine (thorazine) and trifluopromazine)), butyrophenones (e.g., haloperidol (Haldol)), thioxanthene derivatives (e.g., chlorprothixene), and dibenzodiazepines (e.g., clozapine); benzodiazepines; dopaminergic agonists and antagonists e.g., L-DOPA, cocaine, amphetamine, α-methyl-tyrosine, reserpine, tetrabenazine, benzotropine, pargyline; noradrenergic agonists and antagonists e.g., clonidine, phenoxybenzamine, phentolamine, tropolone.

5.9.1. INHIBITORY ANTISENSE, RIBOZYME AMD TRIPLE HELIX APPROACHES

In another embodiment, symptoms of certain fsho05 disorders or neuropsychiatric disorders, such as BAD may be ameliorated by decreasing the level of fsh05 gene expression and/or fsh05 gene product activity by using fsh05 gene sequences in conjunction with well-known antisense, gene "knock-out," ribozyme and/or triple helix methods to decrease the level of fsh05 gene expression. Among the compounds that may exhibit the ability to modulate the activity, expression or synthesis of the fsh05 gene, including the ability to ameliorate the symptoms of a fsh05 disorder or a neuropsychiatric disorder, such as BAD, are antisense, ribozyme, and triple helix molecules. Such molecules may be designed to reduce or inhibit either unimpaired, or if appropriate, mutant target gene activity. Techniques for the production and use of such molecules are well known to those of skill in the art.

Antisense RNA and DNA molecules act to directly block the translation of mRNA by hybridizing to targeted mRNA and preventing protein translation. Antisense approaches involve the design of oligonucleotides that are complementary to a target gene mRNA. The antisense oligonucleotides will bind to the complementary target gene mRNA transcripts and prevent translation. Absolute complementarity, although preferred, is not required.

A sequence "complementary" to a portion of an RNA, as referred to herein, means a sequence having sufficient complementarity to be able to hybridize with the RNA, forming a stable duplex; in the case of double-stranded antisense nucleic acids, a single strand of the duplex DNA may thus be tested, or triplex formation may be assayed. The ability to hybridize will depend on both the degree of complementarity and the length of the antisense nucleic acid. Generally, the longer the hybridizing nucleic acid, the more base mismatches with an RNA it may contain and still form a stable duplex (or triplex, as the case may be). One skilled in the art can ascertain a tolerable degree of mismatch by use of standard procedures to determine the melting point of the hybridized complex.

In one embodiment, oligonucleotides complementary to non-coding regions of the fsh05 gene could be used in an antisense approach to inhibit translation of endogenous fsh05 mRNA. Antisense nucleic acids should be at least six nucleotides in length, and are preferably oligonucleotides ranging from 6 to about 50 nucleotides in length. In specific aspects the oligonucleotide is at least 10 nucleotides, at least 17 nucleotides, at least 25 nucleotides or at least 50 nucleotides.

Regardless of the choice of target sequence, it is preferred that in vitro studies are first performed to quantitate the ability of the antisense oligonucleotide to inhibit gene expression. It is preferred that these studies utilize controls that distinguish between antisense gene inhibition and non-specific biological effects of oligonucleotides. It is also preferred that these studies compare levels of the target RNA or protein with that of an internal control RNA or protein. Additionally, it is envisioned that results obtained using the antisense oligonucleotide are compared with those obtained using a control oligonucleotide. It is preferred that the control oligonucleotide is of approximately the same length as the test oligonucleotide and that the nucleotide sequence of the oligonucleotide differs from the antisense sequence no more than is necessary to prevent specific hybridization to the target sequence.

The oligonucleotides can be DNA or RNA or chimeric mixtures or derivatives or modified versions thereof, single-stranded or double-stranded. The oligonucleotide can be modified at the base moiety, sugar moiety, or phosphate backbone, for example, to improve stability of the molecule, hybridization, etc. The oligonucleotide may include other appended groups such as peptides (e.g., for targeting host cell receptors in vivo), or agents facilitating transport across the cell membrane (see, e.g., Letsinger, et al., 1989, Proc. Natl. Acad. Sci. U.S.A. 86, 6553–6556; Lemaitre, et al., 1987, Proc. Natl. Acad. Sci. 84, 648–652; PCT Publication No. WO88/09810, published Dec. 15, 1988) or the blood-brain barrier (see, e.g., PCT Publication No. WO89/10134, published Apr. 25, 1988), hybridization-triggered cleavage agents (see, e.g., Krol et al., 1988, BioTechniques 6, 958–976) or intercalating agents (see, e.g., Zon, 1988, Pharm. Res. 5, 539–549). To this end, the oligonucleotide may be conjugated to another molecule, e.g., a peptide, hybridization triggered cross-linking agent, transport agent, hybridization-triggered cleavage agent, etc.

The antisense oligonucleotide may comprise at least one modified base moiety which is selected from the group including but not limited to 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3) w, and 2,6-diaminopurine.

The antisense oligonucleotide may also comprise at least one modified sugar moiety selected from the group including but not limited to arabinose, 2-fluoroarabinose, xylulose, and hexose.

In yet another embodiment, the antisense oligonucleotide comprises at least one modified phosphate backbone selected from the group consisting of a phosphorothioate, a phosphorodithioate, a phosphoramidothioate, a phosphoramidate, a phosphordiamidate, a methylphosphonate, an alkyl phosphotriester, and a formacetal or analog thereof.

In yet another embodiment, the antisense oligonucleotide is an α-anomeric oligonucleotide. An α-anomeric oligonucleotide forms specific double-stranded hybrids with complementary RNA in which, contrary to the usual β-units, the strands run parallel to each other (Gautier, et al., 1987, Nucl. Acids Res. 15, 6625–6641). The oligonucleotide is a 2'-O-methylribonucleotide (Inoue, et al., 1987, Nucl. Acids Res. 15, 6131–6148), or a chimeric RNA-DNA analogue (Inoue, et al., 1987, FEBS Lett. 215, 327–330).

Oligonucleotides of the invention may be synthesized by standard methods known in the art, e.g. by use of an automated DNA synthesizer (such as are commercially available from Biosearch, Applied Biosystems, etc.). As examples, phosphorothioate oligonucleotides may be synthesized by the method of Stein, et al. (1988, Nucl. Acids Res. 16, 3209), methylphosphonate oligonucleotides can be prepared by use of controlled pore glass polymer supports (Sarin, et al., 1988, Proc. Natl. Acad. Sci. U.S.A. 85, 7448–7451), etc.

While antisense nucleotides complementary to the target gene coding region sequence could be used, those complementary to the transcribed, untranslated region are most preferred. For example, antisense oligonucleotides having the following sequences can be utilized in accordance with the invention:

```
1) 5'-CTGTAGTTGA-3'                                                    (SEQ ID NO:4)

2) 5'-CTGTAGTTGATAAGTCG-3'                                             (SEQ ID NO:5)

3) 5'-CTGTAGTTGATAAGTCGTCCGGCGA-3'                                     (SEQ ID NO:6)

4) 5'-CTGTAGTTGATAAGTCGTCCGGCGATACTGGGGAGTCAATTCGGAGGGAA-3'            (SEQ ID NO:7)

5) 5'-TGTGACCTTTTTAACATCAACTTAA-3'                                     (SEQ ID NO:8)

6) 5'-TGTGACCTTTTTAACATCAACTTAATGGAGTGAGACAGTTGTCATTCGAC-3'            (SEQ ID NO:9)
```

Antisense molecules should be delivered to cells that express the target gene in vivo. A number of methods have been developed for delivering antisense DNA or RNA to cells; e.g., antisense molecules can be injected directly into the tissue site, or modified antisense molecules, designed to target the desired cells (e.g., antisense linked to peptides or antibodies that specifically bind receptors or antigens expressed on the target cell surface) can be administered systemically.

However, it is often difficult to achieve intracellular concentrations of the antisense sufficient to suppress translation of endogenous mRNAs. Therefore a preferred approach utilizes a recombinant DNA construct in which the antisense oligonucleotide is placed under the control of a strong pol III or pol II promoter. The use of such a construct to transfect target cells in the patient will result in the transcription of sufficient amounts of single stranded RNAs that will form complementary base pairs with the endogenous target gene transcripts and thereby prevent translation of the target gene mRNA. For example, a vector can be introduced e.g., such that it is taken up by a cell and directs the transcription of an antisense RNA. Such a vector can remain episomal or become chromosomally integrated, as long as it can be transcribed to produce the desired antisense RNA. Such vectors can be constructed by recombinant DNA technology methods standard in the art. Vectors can be plasmid, viral, or others known in the art, used for replication and expression in mammalian cells. Expression of the sequence encoding the antisense RNA can be by any promoter known in the art to act in mammalian, preferably human cells. Such promoters can be inducible or constitutive. Such promoters include but are not limited to: the SV40 early promoter region (Bernoist and Chambon, 1981, Nature 290, 304–310), the promoter contained in the 31 long terminal repeat of Rous sarcoma virus (Yamamoto, et al., 1980, Cell 22, 787–797), the herpes thymidine kinase promoter (Wagner, et al., 1981, Proc. Natl. Acad. Sci. U.S.A. 78, 1441–1445), the regulatory sequences of the metallothionein gene (Brinster, et al., 1982, Nature 296, 39–42), etc. Any type of plasmid, cosmid, YAC or viral vector can be used to prepare the recombinant DNA construct which can be introduced directly into the tissue site. Alternatively, viral vectors can be used that selectively infect the desired tissue, in which case administration may be accomplished by another route (e.g., systemically).

Ribozyme molecules designed to catalytically cleave target gene mRNA transcripts can also be used to prevent translation of target gene mRNA and, therefore, expression of target gene product. (See, e.g., PCT International Publication WO90/11364, published Oct. 4, 1990; Sarver, et al., 1990, Science 247, 1222–1225).

Ribozymes are enzymatic RNA molecules capable of catalyzing the specific cleavage of RNA. (For a review, see Rossi, 1994, Current Biology 4, 469–471). The mechanism of ribozyme action involves sequence specific hybridization of the ribozyme molecule to complementary target RNA, followed by an endonucleolytic cleavage event. The composition of ribozyme molecules must include one or more sequences complementary to the target gene mRNA, and must include the well known catalytic sequence responsible for mRNA cleavage. For this sequence, see, e.g., U.S. Pat. No. 5,093,246, which is incorporated herein by reference in its entirety.

While ribozymes that cleave mRNA at site specific recognition sequences can be used to destroy target gene mRNAs, the use of hammerhead ribozymes is preferred. Hammerhead ribozymes cleave mRNAs at locations dictated by flanking regions that form complementary base pairs with the target mRNA. The sole requirement is that the target mRNA have the following sequence of two bases: 5'-UG-3'. The construction and production of hammerhead ribozymes is well known in the art and is described more fully in Myers, 1995, *Molecular Biology and Biotechnology: A Comprehensive Desk Reference*, VCH Publishers, New York, (see especially Figure. 4, page 833) and in Haseloff and Gerlach, 1988, Nature, 334, 585–591, which is incorporated herein by reference in its entirety.

Preferably the ribozyme is engineered so that the cleavage recognition site is located near the 5' end of the target gene mRNA, i.e., to increase efficiency and minimize the intracellular accumulation of non-functional mRNA transcripts.

For example, hammerhead ribozymes having the following sequences can be utilized in accordance with the invention:

1) 5'-UUCGAAACCUAUGUCAAAGCAGGNNN-NCCUGAGNAGUCAGGGAGGCUU-3' (SEQ ID NO:10) which will cleave between nucleotides 48 and 49 in FIGS. 1A–1D.

2) 5'-AAAGGGAGGCUUAACUGAGGGGUCAA-AGCAGGNNNNCCUGAGNAGUCAGCGGCCUGC-UGAAUAGUUGAUGUC-3' (SEQ ID NO:11) which will cleave between nucleotides 25 and 26 in FIG. 1.

The ribozymes of the present invention also include RNA endoribonucleases (hereinafter "Cech-type ribozymes") such as the one that occurs naturally in *Tetrahymena thermophila* (known as the IVS, or L-19 IVS RNA) and that has been extensively described by Thomas Cech and collaborators (Zaug, et al., 1984, Science, 224, 574–578; Zaug and Cech, 1986, Science, 231, 470–475; Zaug, et al., 1986, Nature, 324, 429–433; published International patent application No. WO 88/04300 by University Patents Inc.; Been and Cech, 1986, Cell, 47, 207–216). The Cech-type ribozymes have an eight base pair active site which hybridizes to a target RNA sequence whereafter cleavage of the target RNA takes place. The invention encompasses those Cech-type ribozymes which target eight base-pair active site sequences that are present in the target gene.

As in the antisense approach, the ribozymes can be composed of modified oligonucleotides (e.g., for improved stability, targeting, etc.) and should be delivered to cells that express the target gene in vivo. A preferred method of delivery involves using a DNA construct "encoding" the ribozyme under the control of a strong constitutive pol III or pol II promoter, so that transfected cells will produce sufficient quantities of the ribozyme to destroy endogenous target gene messages and inhibit translation. Because ribozymes unlike antisense molecules, are catalytic, a lower intracellular concentration is required for efficiency.

Endogenous target gene expression can also be reduced by inactivating or "knocking out" the target gene or its promoter using targeted homologous recombination (e.g., see Smithies, et al., 1985, Nature 317, 230–234; Thomas and Capecchi, 1987, Cell 51, 503–512; Thompson, et al., 1989, Cell 5, 313–321; each of which is incorporated by reference herein in its entirety). For example, a mutant, non-functional target gene (or a completely unrelated DNA sequence) flanked by DNA homologous to the endogenous target gene (either the coding regions or regulatory regions of the target gene) can be used, with or without a selectable marker and/or a negative selectable marker, to transfect cells that express the target gene in vivo. Insertion of the DNA construct, via targeted homologous recombination, results in inactivation of the target gene. Such approaches are particularly suited in the agricultural field where modifications to ES (embryonic stem) cells can be used to generate animal offspring with an inactive target gene (e.g., see Thomas and Capecchi, 1987 and Thompson, 1989, supra). However this approach can be adapted for use in humans provided the recombinant DNA constructs are directly administered or targeted to the required site in vivo using appropriate viral vectors.

Alternatively, endogenous target gene expression can be reduced by targeting deoxyribonucleotide sequences complementary to the regulatory region of the target gene (i.e., the target gene promoter and/or enhancers) to form triple helical structures that prevent transcription of the target gene in target cells in the body. (See generally, Helene, 1991, Anticancer Drug Des., 6(6), 569–584; Helene, et al., 1992, Ann. N.Y. Acad. Sci., 660, 27–36; and Maher, 1992, Bioassays 14(12), 807–815).

Nucleic acid molecules to be used in triplex helix formation for the inhibition of transcription should be single stranded and composed of deoxynucleotides. The base composition of these oligonucleotides must be designed to promote triple helix formation via Hoogsteen base pairing rules, which generally require sizeable stretches of either purines or pyrimidines to be present on one strand of a duplex. Nucleotide sequences may be pyrimidine-based, which will result in TAT and CGC$^+$ triplets across the three associated strands of the resulting triple helix. The pyrimidine-rich molecules provide base complementarity to a purine-rich region of a single strand of the duplex in a parallel orientation to that strand. In addition, nucleic acid molecules may be chosen that are purine-rich, for example, contain a stretch of G residues. These molecules will form a triple helix with a DNA duplex that is rich in GC pairs, in which the majority of the purine residues are located on a single strand of the targeted duplex, resulting in GGC triplets across the three strands in the triplex.

Alternatively, the potential sequences that can be targeted for triple helix formation may be increased by creating a so called "switchback" nucleic acid molecule. Switchback molecules are synthesized in an alternating 5'-3', 3'-5' manner, such that they base pair with first one strand of a duplex and then the other, eliminating the necessity for a sizeable stretch of either purines or pyrimidines to be present on one strand of a duplex.

In instances wherein the antisense, ribozyme, and/or triple helix molecules described herein are utilized to inhibit mutant gene expression, it is possible that the technique may so efficiently reduce or inhibit the transcription (triple helix) and/or translation (antisense, ribozyme) of mRNA produced by normal target gene alleles that the possibility may arise wherein the concentration of normal target gene product present may be lower than is necessary for a normal phenotype. In such cases, to ensure that substantially normal levels of target gene activity are maintained, therefore, nucleic acid molecules that encode and express target gene polypeptides exhibiting normal target gene activity may, be introduced into cells via gene therapy methods such as those described, below, in Section 5.9.2 that do not contain sequences susceptible to whatever antisense, ribozyme, or triple helix treatments are being utilized. Alternatively, in instances whereby the target gene encodes an extracellular protein, it may be preferable to co-administer normal target gene protein in order to maintain the requisite level of target gene activity.

Anti-sense RNA and DNA, ribozyme, and triple helix molecules of the invention may be prepared by any method known in the art for the synthesis of DNA and RNA molecules, as discussed above. These include techniques for chemically synthesizing oligodeoxyribonucleotides and oligoribonucleotides well known in the art such as for example solid phase phosphoramidite chemical synthesis. Alternatively, RNA molecules may be generated by in vitro and in vivo transcription of DNA sequences encoding the antisense RNA molecule. Such DNA sequences may be incorporated into a wide variety of vectors that incorporate suitable RNA polymerase promoters such as the T7 or SP6 polymerase promoters. Alternatively, antisense cDNA constructs that synthesize antisense RNA constitutively or inducibly, depending on the promoter used, can be introduced stably into cell lines.

5.9.2. GENE REPLACEMENT THERAPY

With respect to an increase in the level of normal fsh05 gene expression and/or fsh05 gene product activity, fsh05 gene nucleic acid sequences, described, above, in Section 5.1, can, for example, be utilized for the treatment of a fsh05 disorder or a neuropsychiatric disorder, such as BAD. Such treatment can be administered, for example, in the form of gene replacement therapy. Specifically, one or more copies of a normal fsh05 gene or a portion of the fsh05 gene that directs the production of a fsh05 gene product exhibiting normal fsh05 gene function, may be inserted into the appropriate cells within a patient, using vectors that include, but are not limited to adenovirus, adeno-associated virus, and retrovirus vectors, in addition to other particles that introduce DNA into cells, such as liposomes.

Because the fsh05 gene is expressed in the brain, such gene replacement therapy techniques should be capable delivering fsh05 gene sequences to these cell types within patients. Thus, in one embodiment, techniques that are well known to those of skill in the art (see, e.g., PCT Publication No. WO89/10134, published Apr. 25, 1988) can be used to enable fsh05 gene sequences to cross the blood-brain barrier readily and to deliver the sequences to cells in the brain. With respect to delivery that is capable of crossing the blood-brain barrier, viral vectors such as, for example, those described above, are preferable.

In another embodiment, techniques for delivery involve direct administration of such fsh05 gene sequences to the site of the cells in which the fsh05 gene sequences are to be expressed.

Additional methods that may be utilized to increase the overall level of fsh05 gene expression and/or fsh05 gene product activity include the introduction of appropriate fsh05-expressing cells, preferably autologous cells, into a patient at positions and in numbers that are sufficient to ameliorate the symptoms of a fsh05 disorder or a neuropsychiatric disorder, such as BAD. Such cells may be either recombinant or non-recombinant.

Among the cells that can be administered to increase the overall level of fsh05 gene expression in a patient are normal cells, preferably brain cells, that express the fsh05 gene.

Alternatively, cells, preferably autologous cells, can be engineered to express fsh05 gene sequences, and may then be introduced into a patient in positions appropriate for the amelioration of the symptoms of a fsh05 disorder or a neuropsychiatric disorder, such as BAD. Alternately, cells that express an unimpaired fsh05 gene and that are from a MHC matched individual can be utilized, and may include, for example, brain cells. The expression of the fsh05 gene sequences is controlled by the appropriate gene regulatory sequences to allow such expression in the necessary cell types. Such gene regulatory sequences are well known to the skilled artisan. Such cell-based gene therapy techniques are well known to those skilled in the art, see, e.g., Anderson, U.S. Pat. No. 5,399,349.

When the cells to be administered are non-autologous cells, they can be administered using well known techniques that prevent a host immune response against the introduced cells from developing. For example, the cells may be introduced in an encapsulated form which, while allowing for an exchange of components with the immediate extracellular environment, does not allow the introduced cells to be recognized by the host immune system.

Additionally, compounds, such as those identified via techniques such as those described, above, in Section 5.8, that are capable of modulating fsh05 gene product activity can be administered using standard techniques that are well known to those of skill in the art. In instances in which the compounds to be administered are to involve an interaction with brain cells, the administration techniques should include well known ones that allow for a crossing of the blood-brain barrier.

5.10. PHARMACEUTICAL PREPARATIONS AND METHODS OF ADMINISTRATION

The compounds that are determined to affect fsh05 gene expression or gene product activity can be administered to a patient at therapeutically effective doses to treat or ameliorate a fsh05 disorder or a neuropsychiatric disorder, such as BAD. A therapeutically effective dose refers to that amount of the compound sufficient to result in amelioration of symptoms of such a disorder.

5.10.1. EFFECTIVE DOSE

Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds that exhibit large therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the $IC_{50}$ (i.e., the concentration of the test compound that achieves a half-maximal inhibition of symptoms) as determined in cell culture. Such information can be used to more accurately determine useful doses in humans. Levels in plasma may be measured, for example, by high performance liquid chromatography.

5.10.2. FORMULATIONS AND USE

Pharmaceutical compositions for use in accordance with the present invention may be formulated in conventional manner using one or more physiologically acceptable carriers or excipients.

Thus, the compounds and their physiologically acceptable salts and solvates may be formulated for administration by inhalation or insufflation (either through the mouth or the nose) or oral, buccal, parenteral or rectal administration.

For oral administration, the pharmaceutical compositions may take the form of, for example, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations may also contain buffer salts, flavoring, coloring and sweetening agents as appropriate.

Preparations for oral administration may be suitably formulated to give controlled release of the active compound.

For buccal administration the compositions may take the form of tablets or lozenges formulated in conventional manner.

For administration by inhalation, the compounds for use according to the present invention are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g., gelatin for use in an inhaler or insufflator may be formulated containing a powder mix of the compound and a suitable powder base such as lactose or starch.

The compounds may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen-free water, before use.

The compounds may also be formulated in rectal compositions such as suppositories or retention enemas, e.g., containing conventional suppository bases such as cocoa butter or other glycerides.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

The compositions may, if desired, be presented in a pack or dispenser device that may contain one or more unit dosage forms containing the active ingredient. The pack may for example comprise metal or plastic foil, such as a blister pack. The pack or dispenser device may be accompanied by instructions for administration.

6. EXAMPLE

IDENTIFICATION AND CLONING OF THE fsh05 GENE

In the Example presented in this Section, studies are described that, first, define an interval approximately 500 kb on the long arm of human chromosome 18 within which a region associated with a neuropsychiatric disorder is located and, second, identify and clone a novel gene, referred to herein as fsh05, which lies within this region and which can be involved in neuropsychiatric disorders.

6.1. MATERIALS AND METHODS

Linkage Disequilibrium. Linkage disequilibrium (LD) studies were performed using DNA from a population sample of neuropsychiatric disorder (BP-I) patients. The population sample and LD techniques were as described in Friemer et al., 1996, Nature Genetics 12:436–441. The present LD study took advantage of the additional physical markers identified via the physical mapping techniques described below.

Yeast artificial chromosome (YAC) mapping. For physical mapping, yeast artificial chromosomes (YACs) containing human sequences were mapped to the region being analyzed based on publicly available maps (Cohen et al., 1993, C.R. Acad. Sci. 316, 1484–1488). The YACs were then ordered and contig reconstructed by performing standard short tag sequence (STS)-content mapping with microsatellite markers and non-polymorphic STSs available from databases that surround the genetically defined candidate region.

Bacterial artificial chromosome (BAC) mapping. The STSs from the region were used to screen a human BAC library (Research Genetics, Huntsville, Ala.). The ends of the BACs were cloned or directly sequenced. The end sequences were used to amplify the next overlapping BACs. From each BAC, additional microsatellites were identified. Specifically, random sheared libraries were prepared from overlapping BACs within the defined genetic interval. BAC DNA was sheared with a nebulizer (CIS-US Inc., Bedford, Mass.). Fragments in the size range of 600 to 1,000 bp were utilized for the sublibrary production. Microsatellite sequences from the sublibraries were identified by corresponding microsatellite probes. Sequences around such repeats were obtained to enable development of PCR primers for genomic DNA.

Radiation hybrid (RH) mapping. Standard RH mapping techniques were applied to a Stanford G3 RH mapping panel (Research Genetics, Huntsville, Ala.) to order all microsatellite markers and non-polymorphic STSs in the region being analyzed.

Sample sequencing. Random sheared libraries were made from all the BACs within the defined genetic region. Approximately 6,000 subclones within the approximately 500 kb region were sequenced with vector primers in order to achieve a 6-fold sequence coverage of the region. All sequences were processed through an automated sequence analysis pipeline that assessed quality, removed vector sequences and masked repetitive sequences. The resulting sequences were then compared to public DNA and protein databases using BLAST algorithms (Altschul, et al., 1990, J. Mclec. Biol., 215, 403–410).

cDNA selection. cDNA selection was used as an additional method for gene identification of transcribed sequences over large regions of the genome. Through a combination of characterizations including physical mapping and RNA hybridization, the selected cDNAs were arranged into transcription units. The cDNA selection technique was carried out as described by Rommens, et al. (1994, in *Identification of Transcribed Sequences*, Hochgeschwender and Gardiner, eds., Plenum Press, New York, pp. 65–79).

Transcription mapping. The combination of sample sequencing and cDNA selection were arranged into tentative transcription units which provided the framework for a detailed transcription map of the genomic region of interest. cDNA library. A human fetal brain cDNA library was purchased Clontech (Palo Alto, Calif.) and screened according to manufacturer's recommendations.

Northern analysis. Standard Northern analysis techniques were utilized in probing human and fetal multiple tissue Northern blots purchased from Clontech (Palo Alto, CA). Blots were hybridized to a 777 bp probe, which was derived by PCR from a fsh05 cDNA sequence.

6.2. RESULTS

Genetic regions involved in bipolar affective disorder (BAD) human genes had previously been reported to map to portions of the long (18q) and short (18p) arms of human chromosome 18, including a broad 18q genetic region of about 6–7 cM between markers D18S469 and D18S554 (U.S. Provisional Applications Ser. Nos. 60/014,498 and 60/023,438, filed on Mar. 28, 1996 and Aug. 23, 1996, respectively, the entire contents of each of which are incorporated herein by reference; Freimer, et al., 1996, Neuropsychiat. Genet. 67, 254–263; Freimer, et al., 1996, Nature Genetics 12, 436–441), the entire contents of each of which are incorporated herein by reference.

Prior to attempting to identify gene sequences, studies were performed to further narrow the neuropsychiatric disorder region. Specifically, a linkage disequilibrium (LD) analysis was performed using population samples and techniques as described in Section 6.1, above, which took advantage of the additional physical markers identified via the physical mapping techniques described below.

In order to provide the precise order of genetic markers necessary for linkage and LD mapping, and to guide new microsatellite marker development for finer mapping, a high resolution physical map of the 18q23 candidate region was developed using YAC, BAC and RH techniques.

For such physical mapping, first, YACs were mapped to the chromosome 18 region being analyzed. Using the mapped YAC contig as a framework, the region from publicly available markers D18S1161 and D18S554, which spans most of the D18S469-D18S554 region described above, was also mapped and contiged with BACs. Sublibraries from the contiged BACs were constructed, from which microsatellite marker sequences were identified and sequenced.

To ensure development of an accurate physical map, the radiation hybrid (RH) mapping technique was independently applied to the region being analyzed. RH was used to order all microsatellite markers and non-polymorphic STSs in the region. Thus, the high resolution physical map ultimately constructed was obtained using data from RH mapping and STS-content mapping.

The new markers identified via physical mapping were typed in an LD analysis of samples collected from families affected with bipolar affective disorder. One interpretation of the results of this LD analysis narrows down the chromosome 18 long arm region within which a gene involved in neuropsychiatric disorders lies to an interval of about 500 kb between the publicly available markers D18S1121 and D18S380.

The BAC clones within the newly identified 500 kb neuropsychiatric disorder region were further analyzed to identify specific genes within the region. A combination of sample sequencing, cDNA selection and transcription mapping analyses were combined to arrange sequences into tentative transcription units, that is, tentatively delineating the coding sequences of genes within this genomic region of interest.

One of the transcription units identified was termed fsh05. The corresponding fsh05 gene can, therefore, can be involved in neuropsychiatric disorders.

fsh05 cDNA clones were isolated through screening and random sequencing of a human fetal brain cDNA library. Among the cDNA clones identified were FSH5-1 (ATCC accession No. 98317)and FSH5-2 (ATCC accession No. 98318). Upon further analysis of genomic sequences, it was determined that the full length fsh05 gene sequence is contained within BAC54 (Identification Reference EpHS996, ATCC Accession No. 98363).

fsh05 nucleotide and amino acid sequences are shown in FIG. 1. The fsh05 gene product sequence depicted in FIG. 1 exhibits some amino acid sequence similarity with two known genes identified from other distantly related species. First, the depicted portion of the fsh05 gene product exhibits approximately 45% amino acid sequence similarity with a 295 amino acid residue portion of P36, a possible *Leishmania amazonensis* quinone oxidoreductase (Liu and Chang, 1994, Mol. Biochem. Parasitol. 66, 201–120). The depicted portion of the fsh05 gene product also exhibits approximately 45% amino acid sequence similarity with a 292 amino acid portion of ARP, an *Arabidopsis thaliana* NADPH oxidoreductase homolog (Babiychuk, et al., 1995, J. Biol. Chem. 270, 26224–26231). In addition, a portion (primarily non-coding) of the depicted fsh05 nucleotide sequence, was found to exhibit similarity to EST U55988.

Northern analysis was used to examine fsh05 expression. The Northern analysis revealed that fsh05 appears to be expressed in adult heart, brain, placenta, lung, liver, skeletal muscle, kidney, pancreas, and in fetal brain, lung, liver, and kidney. Bands of 6 kb and 4 kb were seen in all the above tissues.

7. DEPOSIT OF MICROORGANISMS

The following microorganisms were deposited with the American Type Culture Collection (ATCC), Rockville, Md., on the date indicated and assigned the indicated accession number:

| Microorganism | ATCC Accession No. | Date of Deposit |
| --- | --- | --- |
| FSH5-1 | ATCC 98317 | February 7, 1997 |
| FSH5-2 | ATCC 98318 | February 7, 1997 |
| EpHS996 | ATCC 98363 | March 19, 1997 |

The present invention is not to be limited in scope by the specific embodiments described herein, which are intended as single illustrations of individual aspects of the invention, and functionally equivalent methods and components are within the scope of the invention. Indeed, various modifications of the invention, in addition to those shown and described herein will become apparent to those skilled in the art from the foregoing description and accompanying drawings. Such modifications are intended to fall within the scope of the appended claims.

All publications and patent applications mentioned in this specification are herein incorporated by reference to the same extent as if each individual publication or patent application was specifically and individually indicated to be incorporated by reference.

What is claimed is:

1. An isolated nucleic acid molecule comprising a nucleotide sequence which encodes a protein comprising the amino acid sequence of SEQ ID NO:2.

2. The isolated nucleic acid molecule of claim 1 which encodes a protein comprises the sequence of SEQ. ID. NO.:1.

3. The isolated nucleic acid molecule of claim 1, wherein said nucleic acid molecule is the cDNA insert in ATCC deposit ATCC98317.

4. The isolated nucleic acid molecule of claim 1, wherein said nucleic acid molecule is the coding sequence of the cDNA insert contained in ATCC deposit ATCC98318.

5. A vector comprising the isolated nucleic acid molecule of claim 1.

6. A vector comprising the isolated nucleic acid molecule of claim 2.

7. An isolated host cell line transformed to contain the nucleic acid of claim 1.

8. An isolated host cell line transformed to contain the nucleic acid of claim 2.

9. An isolated host cell line transformed to contain the nucleic acid of claim 5.

10. An isolated host cell line transformed to contain the nucleic acid of claim 6.

11. An isolated nucleic acid molecule comprising a nucleotide sequence which encodes a human allelic variant of a protein comprising the amino acid sequence of SEQ ID NO:2, wherein said human allelic variant is encoded by a nucleic acid molecule that hybridizes under stringent conditions to the complement SEQ ID NO:1, wherein said stringent conditions comprise hybridization in 0.5 M NaHPO$_y$, 7% sodium dodecyl sulfate, 1 mM EDTA at 68° C., and washing in 0.1×SSC/0.1% at 68° C. under stringent conditions.

12. A vector comprising the isolated nucleic acid molecule of claim 11.

13. An isolated host cell line transformed to contain the nucleic acid of claim 11.

14. An isolated host cell line transformed to contain the nucleic acid of claim 12.

15. A genetically engineered host cell line that contains the nucleotide sequence of claim 1, 2, 3, 4 or 11 in operative association with a nucleotide regulatory sequence that controls expression of the nucleotide sequence in the host cell line.

* * * * *

SEQUENCE LISTING (1) GENERAL INFORMATION:

(iii) NUMBER OF SEQUENCES: 11

(2) INFORMATION FOR SEQ ID NO:1:

(i) SEQUENCE CHARACTERISTICS:
      (A) LENGTH: 3794 base pairs
      (B) TYPE: nucleic acid
      (C) STRANDEDNESS: single
      (D) TOPOLOGY: linear (ii) MOLECULE TYPE: DNA (ix) FEATURE:
      (A) NAME/KEY: Coding Sequence
      (B) LOCATION: 1...900
      (D) OTHER INFORMATION:
      (A) NAME/KEY: Fsh 05 gene
      (B) LOCATION: 1...3794
      (D) OTHER INFORMATION:

(xi) SEQUENCE DESCRIPTION: SEQ ID NO:1:

```
GAC ATC AAC TAT TCA GCA GGC CGC TAT GAC CCC TCA GTT AAG CCT CCC        48
Asp Ile Asn Tyr Ser Ala Gly Arg Tyr Asp Pro Ser Val Lys Pro Pro
 1               5                  10                  15
```

-continued

| | | |
|---|---|---|
| TTT GAC ATA GGT TTC GAA GGC ATT GGG GAG GTG GTG GCC CTA GGC CTC<br>Phe Asp Ile Gly Phe Glu Gly Ile Gly Glu Val Val Ala Leu Gly Leu<br>          20                   25                      30 | 96 |
| TCT GCT AGT GCC AGA TAC ACA GTT GGC CAA GCT GTG GCT TAC ATG GCA<br>Ser Ala Ser Ala Arg Tyr Thr Val Gly Gln Ala Val Ala Tyr Met Ala<br>        35                   40                   45 | 144 |
| CCT GGT TCT TTT GCT GAG TAC ACA GTT GTG CCT GCC AGC ATT GCA ACT<br>Pro Gly Ser Phe Ala Glu Tyr Thr Val Val Pro Ala Ser Ile Ala Thr<br>50                   55                   60 | 192 |
| CCA GTG CCC TCA GTG AAA CCC GAG TAT CTT ACC CTG CTG GTA AGT GGC<br>Pro Val Pro Ser Val Lys Pro Glu Tyr Leu Thr Leu Leu Val Ser Gly<br>65                   70                   75                  80 | 240 |
| ACC ACC GCA TAC ATC AGC CTG AAA GAG CTC GGA GGA CTG TCG GAA GGG<br>Thr Thr Ala Tyr Ile Ser Leu Lys Glu Leu Gly Gly Leu Ser Glu Gly<br>                 85                   90                   95 | 288 |
| AAA AAA GTT TTG GTG ACA GCA GCA GCT GGG GGA ACG GGC CAG TTT GCC<br>Lys Lys Val Leu Val Thr Ala Ala Ala Gly Gly Thr Gly Gln Phe Ala<br>            100                  105                110 | 336 |
| ATG CAG CTT TCA AAG AAG GCA AAG TGC CAT GTA ATT GGA ACC TGC TCT<br>Met Gln Leu Ser Lys Lys Ala Lys Cys His Val Ile Gly Thr Cys Ser<br>            115                  120                125 | 384 |
| TCT GAT GAA AAG TCT GCT TTT CTG AAA TCT CTT GGC TGT GAT CGT CCT<br>Ser Asp Glu Lys Ser Ala Phe Leu Lys Ser Leu Gly Cys Asp Arg Pro<br>130                   135                  140 | 432 |
| ATC AAC TAT AAA ACT GAA CCC GTA GGT ACC GTC CTT AAG CAG GAG TAC<br>Ile Asn Tyr Lys Thr Glu Pro Val Gly Thr Val Leu Lys Gln Glu Tyr<br>145                   150                  155                160 | 480 |
| CCT GAA GGT GTC GAT GTG GTC TAT GAA TCT GTT GGG GGA GCC ATG TTT<br>Pro Glu Gly Val Asp Val Val Tyr Glu Ser Val Gly Gly Ala Met Phe<br>                  165                  170                175 | 528 |
| GAC TTG GCT GTA GAC GCC CTG GCT ACG AAA GGG CGC TTG ATA GTA ATA<br>Asp Leu Ala Val Asp Ala Leu Ala Thr Lys Gly Arg Leu Ile Val Ile<br>                180                  185                190 | 576 |
| GGG TTT ATC TCT GGC TAC CAA ACT CCT ACT GGC CTT TCG CCT GTG AAA<br>Gly Phe Ile Ser Gly Tyr Gln Thr Pro Thr Gly Leu Ser Pro Val Lys<br>            195                  200                205 | 624 |
| GCA GGA ACA TTG CCA GCC AAA CTG CTC AAG AAA TCT GCC AGC GTA CAG<br>Ala Gly Thr Leu Pro Ala Lys Leu Leu Lys Lys Ser Ala Ser Val Gln<br>            210                  215                220 | 672 |
| GGC TTC TTC CTG AAC CAT TAC CTT TCT AAG TAT CAA GCA GCC ATG AGC<br>Gly Phe Phe Leu Asn His Tyr Leu Ser Lys Tyr Gln Ala Ala Met Ser<br>225                   230                  235                240 | 720 |
| CAC TTG CTC GAG ATG TGT GTG AGC GGA GAC CTG GTT TGT GAG GTG GAC<br>His Leu Leu Glu Met Cys Val Ser Gly Asp Leu Val Cys Glu Val Asp<br>                245                  250                255 | 768 |
| CTT GGA GAT CTG TCT CCA GAG GGC AGG TTT ACT GGC CTG GAG TCC ATA<br>Leu Gly Asp Leu Ser Pro Glu Gly Arg Phe Thr Gly Leu Glu Ser Ile<br>            260                  265                270 | 816 |
| TTC CGT GCT GTC AAT TAT ATG TAC ATG GGG AAA AAC ACT GGA AAA ATT<br>Phe Arg Ala Val Asn Tyr Met Tyr Met Gly Lys Asn Thr Gly Lys Ile<br>            275                  280                285 | 864 |
| GTA GTT GAA TTA CCT CAC TCT GTC AAC AGT AAG CTG TAA AAACAGA ACAATG<br>Val Val Glu Leu Pro His Ser Val Asn Ser Lys Leu<br>290                   295                  300 | 916 |
| ACATAATCAA GGGAGAAAGA AAATGGGCAC TTTATGTCTC AGAATTACTC AAATCAATTT | 976 |
| ATTTTTAGTT GGTAATGGAT ATAATATTTC TTAAAACAAA AGTAAGGTGT TAATGAATAG | 1036 |
| GTCTCTCCTT CTCCTCCTCC TCCTCCTCTT CCCTTGGGGG AAAAAAAAAA ATGTGCTAAT | 1096 |
| AAAACCTCGT GCCATGGCTA AGAGGGAAAA CGCTTACATT CAATTCTTTA GTCATGGATG | 1156 |

```
GTCTCGTTCC AGATGTTATT GTTCCAGGGA ACTAAATTCA TTCCTGATGC CAGATCTGAT    1216

CGAGTCAGTA TGTCTTCAGC TTGATCAGAT TTTAAAATCA GTTTTGAAAG TGGTTCCCGA    1276

CTTCTTTGCT TTGGGAGAAT TTGGTCTTAT GCTCATAAGC AGTTCATGAG TGACAAGTGT    1336

AGCAAAAGCC AGCCATATAT TTTCAGAATC TATATCCTCA GGAAATGGTC CTTTTTTTTT    1396

CTATAAATCA CCAACCAACT ATCTAAATGG ACATTTGGGG GAATTCCCTC CCAAATTTGA    1456

TTTTGTTATT AGAAAAATGA TTCCGTGAAC ACAGATGTGT TTTGAAGAAG TAGCACGTAA    1516

TGGCTTTTAT CTACCATCAA CCTGATAAGG CACATGTGAA ATGGAAATGT TCTCTTTCCT    1576

CTGAAGCAGC AAATTAATGT TGAAAACTTA CATAGACAGA AAGTAGGTTT TGGAAAGGGA    1636

AACCACAGAG ATTAGGGGGA CTTAAAATTA ATATAGGCAC AGGAAAGAGA AAAGTGTGCG    1696

CTCCATTCTC AGTGGGGGTC ACCACAAAAC ACGGGCCCAG GAGGGAAGCG CTGTCTAGGC    1756

ACACGGCAAG GCCTTAGTAA CAGCATGCTA CACTGCTCGA GGTACGGTAT GTCCCATCGC    1816

CCTGTGCACC GTAGAGACCT CAGTCATCTC AAGGAAGAAT ACATTTGCTT CTCCTTAGAG    1876

GCGTTCGAAC TAGAAGCTAT GCGTTACCTC TGATCTGGAA ACAGAATAGC AGCCACTCAT    1936

TCTGCATTCC CATTTTTCTC TCCACGTGTT CTGGTGAATG GAGATGCTCC TTGGCACTAT    1996

AGCCTGATGT CCCACATTGA CCCACTGACC ACACAGGAAA AGCAGCGAAA CCTGCACCCT    2056

CTCTTCTGAG TCCAGCCTGT GGCTCATCGG CTTCCCTCTT AACCTTTAGT GCCCTGAAGA    2116

CTGCTGCCGC TGTCACCGTT GCGCTGAAAC CCCATGGGCC CGTTCTGATT GAAGGTGAAG    2176

CCCACCAGAT TATTTTTCAA AGTCTTAGGT TTCGGTGTAT CTAACCTGCT CAGTAAATAT    2236

GGACGCAATT AAAGATGCTC TAGGAAATTT GGGGACTGTA TTTAATTTTT CTTTCCTTCC    2296

ATCTGAGGAG CAGGAATCCT ACTGCTGAAT AGCTGTTAGT ATCTATTTTA CAGATTTACT    2356

CATTTTCAGG TACCTAATGT AGCTGCTAGC ATGCATGCAC ACAATTCAAT TTATATGGTA    2416

AATGGAACCA AATAATGGCT TCACTGAATG TTATGGCTGC ACTGAAGGGA AATGTCACGG    2476

TAAATAGCTG CCAAATTATG GATCATGCCG AAGTGTCACA ACTGCACTAA AGACAAATAG    2536

CGACTAGAGG CTATTGCCAC TGTGACGCTT TTGAGTTATG AAGAAGGGTA GCGGCCTGAT    2596

GCGAGGCTCT TTGTGTCCTC ATTATAGCAA AGGGTTACTG GTGCAGGGGA CTAGGAAAAA    2656

CCCGTCCAGT GTGGTGCTTA GTTATTCATC CATCCCTTTC AGACCTAACG AGCCACAGCC    2716

ACACGGAAAG AGACTTTGCC TCACTTTTAC ATTCACAAAC AAACAAAGGA GGGGGGAGCA    2776

GGTTTTATGA ATGTAACTGT GCACAGGAAA TGACTGGTAA TGGAAAAAAT GTTGTAATAA    2836

AATAATCTAA TCAAAGAATA TTATTAAATT TAACATAGTC TATGTCCAAA AGGCTTAGTT    2896

GCTTCTTATG CAGATAGATG TGTGAAATNT AAGCAGTAAT GTACTTTCTC CCTTTGTAAA    2956

GACTTGGGGA GTAAGGACAT TACCAACTAA ATTGCTTCTT CGAAACTGAA GTGAGTCCCG    3016

GTTTGTTTCA TTTTAATGGG AGGGTAATAA AGATGAAAGA CCAACATTTT AACTGATGGA    3076

TCCCTTAAGC TACAGAATAG AAATTTATTG TGTTTTGAGG GAATATACTA AATGCAGCTA    3136

TGTAAAAATA AAATTCAAAC GCCCAGGATT AAAATAAAAT ATAATCTGAA AACCTCATGT    3196

TCTCTCTTTC CCCAAACTAA GAAAGTGCAC TGCATGCTGT TTTCACTTAT TCTTAGAAAA    3256

CAAGCATGAA AGATTCCTCC CATTCAGATA ATGCCAAAAA TATGTTTAAA CTTTTTTTTA    3316

TTCTTTTGAA AAATGATTTG TAAATTGAGG GTCATAGTTC AGCATCAGTT TCATCTTCTG    3376

GGATTATTGT TCAAGACCAG CCTCTAATGG GAGGTGAAAC GGTACGATGG TCTCAACACC    3436

TTTCTTCTGA ACTGTAATAC ATATCACAAA AAGTACATCC ATAATTCAGG GCAATTGTCA    3496

GTCTTTTTAG AGAAGGGGCC AGGGTGGAAC AATCCCAGTG AGTAAATTAT TTCTCAGCGT    3556
```

```
GGACTTCTCT GCATGTCGGG CTTAGGGTCA CCAGCCGGGC AGGGTGGAAG GAGCTTGCTT    3616

CTTTGAGAAA CCAAGGAGTC CCAGTGATCT GTTACCATTT GGTTATGACT TCTAAAGAGC    3676

CAAATGCTAT TCCTTCAAGC CTGTTTTGCA GGCAGAAAAT ACCAGCAGTG TCATTTAGGG    3736

GTTCCTTTGA TGATGACTAC TGCTGTTAAC TGACCTCAGC AAAAAAAAAA AAAAAAA       3794
```

(2) INFORMATION FOR SEQ ID NO:2:

(i) SEQUENCE CHARACTERISTICS:
        (A) LENGTH: 300 amino acids
        (B) TYPE: amino acid
        (C) STRANDEDNESS: single
        (D) TOPOLOGY: linear (ii) MOLECULE TYPE: protein (v) FRAGMENT TYPE: internal (xi) SEQUENCE DESCRIPTION: SEQ ID NO:2:

```
Asp Ile Asn Tyr Ser Ala Gly Arg Tyr Asp Pro Ser Val Lys Pro Pro
 1               5                  10                  15

Phe Asp Ile Gly Phe Glu Gly Ile Gly Glu Val Val Ala Leu Gly Leu
            20                  25                  30

Ser Ala Ser Ala Arg Tyr Thr Val Gly Gln Ala Val Ala Tyr Met Ala
        35                  40                  45

Pro Gly Ser Phe Ala Glu Tyr Thr Val Pro Ala Ser Ile Ala Thr
    50                  55                  60

Pro Val Pro Ser Val Lys Pro Glu Tyr Leu Thr Leu Val Ser Gly
65                  70                  75                  80

Thr Thr Ala Tyr Ile Ser Leu Lys Glu Leu Gly Gly Leu Ser Glu Gly
                85                  90                  95

Lys Lys Val Leu Val Thr Ala Ala Ala Gly Gly Thr Gly Gln Phe Ala
            100                 105                 110

Met Gln Leu Ser Lys Lys Ala Lys Cys His Val Ile Gly Thr Cys Ser
        115                 120                 125

Ser Asp Glu Lys Ser Ala Phe Leu Lys Ser Leu Gly Cys Asp Arg Pro
    130                 135                 140

Ile Asn Tyr Lys Thr Glu Pro Val Gly Thr Val Leu Lys Gln Glu Tyr
145                 150                 155                 160

Pro Glu Gly Val Asp Val Val Tyr Glu Ser Val Gly Gly Ala Met Phe
                165                 170                 175

Asp Leu Ala Val Asp Ala Leu Ala Thr Lys Gly Arg Leu Ile Val Ile
            180                 185                 190

Gly Phe Ile Ser Gly Tyr Gln Thr Pro Thr Gly Leu Ser Pro Val Lys
        195                 200                 205

Ala Gly Thr Leu Pro Ala Lys Leu Leu Lys Lys Ser Ala Ser Val Gln
    210                 215                 220

Gly Phe Phe Leu Asn His Tyr Leu Ser Lys Tyr Gln Ala Ala Met Ser
225                 230                 235                 240

His Leu Leu Glu Met Cys Val Ser Gly Asp Leu Val Cys Glu Val Asp
                245                 250                 255

Leu Gly Asp Leu Ser Pro Glu Gly Arg Phe Thr Gly Leu Glu Ser Ile
            260                 265                 270

Phe Arg Ala Val Asn Tyr Met Tyr Met Gly Lys Asn Thr Gly Lys Ile
        275                 280                 285

Val Val Glu Leu Pro His Ser Val Asn Ser Lys Leu
    290                 295                 300
```

(2) INFORMATION FOR SEQ ID NO:3:

(i) SEQUENCE CHARACTERISTICS:
        (A) LENGTH: 900 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: Other
        (B) LOCATION: 1...900
        (D) OTHER INFORMATION: Open reading frame of Fsh 05 gene (xi) SEQUENCE DESCRIPTION: SEQ ID NO:3:

```
GACATCAACT ATTCAGCAGG CCGCTATGAC CCCTCAGTTA AGCCTCCCTT TGACATAGGT      60

TTCGAAGGCA TTGGGGAGGT GGTGGCCCTA GGCCTCTCTG CTAGTGCCAG ATACACAGTT     120

GGCCAAGCTG TGGCTTACAT GGCACCTGGT TCTTTTGCTG AGTACACAGT TGTGCCTGCC     180

AGCATTGCAA CTCCAGTGCC CTCAGTGAAA CCCGAGTATC TTACCCTGCT GGTAAGTGGC     240

ACCACCGCAT ACATCAGCCT GAAAGAGCTC GGAGGACTGT CGGAAGGGAA AAAAGTTTTG     300

GTGACAGCAG CAGCTGGGGG AACGGGCCAG TTTGCCATGC AGCTTTCAAA GAAGGCAAAG     360

TGCCATGTAA TTGAACCTG CTCTTCTGAT GAAAAGTCTG CTTTTCTGAA ATCTCTTGGC     420

TGTGATCGTC CTATCAACTA TAAAACTGAA CCCGTAGGTA CCGTCCTTAA GCAGGAGTAC     480

CCTGAAGGTG TCGATGTGGT CTATGAATCT GTTGGGGGAG CCATGTTTGA CTTGGCTGTA     540

GACGCCCTGG CTACGAAAGG GCGCTTGATA GTAATAGGGT TTATCTCTGG CTACCAAACT     600

CCTACTGGCC TTTCGCCTGT GAAAGCAGGA ACATTGCCAG CCAAACTGCT CAAGAAATCT     660

GCCAGCGTAC AGGGCTTCTT CCTGAACCAT TACCTTTCTA AGTATCAAGC AGCCATGAGC     720

CACTTGCTCG AGATGTGTGT GAGCGGAGAC CTGGTTTGTG AGGTGGACCT TGGAGATCTG     780

TCTCCAGAGG GCAGGTTTAC TGGCCTGGAG TCCATATTCC GTGCTGTCAA TTATATGTAC     840

ATGGGGAAAA ACACTGGAAA AATTGTAGTT GAATTACCTC ACTCTGTCAA CAGTAAGCTG     900
```

(2) INFORMATION FOR SEQ ID NO:4:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: Antisense oligonucleotide
        (B) LOCATION: 1...10
        (D) OTHER INFORMATION:

(xi) SEQUENCE DESCRIPTION: SEQ ID NO:4:

```
CTGTAGTTGA                                                             10
```

(2) INFORMATION FOR SEQ ID NO:5:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (ix) FEATURE:

(A) NAME/KEY: Antisense oligonucleotide
            (B) LOCATION: 1...17
            (D) OTHER INFORMATION:

(xi) SEQUENCE DESCRIPTION: SEQ ID NO:5:

CTGTAGTTGA TAAGTCG                                                          17

(2) INFORMATION FOR SEQ ID NO:6:

(i) SEQUENCE CHARACTERISTICS:
            (A) LENGTH: 25 base pairs
            (B) TYPE: nucleic acid
            (C) STRANDEDNESS: single
            (D) TOPOLOGY: linear (ii) MOLECULE TYPE: DNA (ix) FEATURE:
            (A) NAME/KEY: Antisense oligonucleotide
            (B) LOCATION: 1...25
            (D) OTHER INFORMATION:

(xi) SEQUENCE DESCRIPTION: SEQ ID NO:6:

CTGTAGTTGA TAAGTCGTCC GGCGA                                                 25

(2) INFORMATION FOR SEQ ID NO:7:

(i) SEQUENCE CHARACTERISTICS:
            (A) LENGTH: 50 base pairs
            (B) TYPE: nucleic acid
            (C) STRANDEDNESS: single
            (D) TOPOLOGY: linear (ii) MOLECULE TYPE: DNA (ix) FEATURE:
            (A) NAME/KEY: Antisense oligonucleotide
            (B) LOCATION: 1...50
            (D) OTHER INFORMATION:

(xi) SEQUENCE DESCRIPTION: SEQ ID NO:7:

CTGTAGTTGA TAAGTCGTCC GGCGATACTG GGGAGTCAAT TCGGAGGGAA                      50

(2) INFORMATION FOR SEQ ID NO:8:

(i) SEQUENCE CHARACTERISTICS:
            (A) LENGTH: 25 base pairs
            (B) TYPE: nucleic acid
            (C) STRANDEDNESS: single
            (D) TOPOLOGY: linear (ii) MOLECULE TYPE: DNA (ix) FEATURE:
            (A) NAME/KEY: Antisense oligonucleotide
            (B) LOCATION: 1...25
            (D) OTHER INFORMATION:

(xi) SEQUENCE DESCRIPTION: SEQ ID NO:8:

TGTGACCTTT TTAACATCAA CTTAA                                                 25

(2) INFORMATION FOR SEQ ID NO:9:

(i) SEQUENCE CHARACTERISTICS:
            (A) LENGTH: 50 base pairs
            (B) TYPE: nucleic acid
            (C) STRANDEDNESS: single
            (D) TOPOLOGY: linear (ii) MOLECULE TYPE: DNA (ix) FEATURE:

-continued

```
        (A) NAME/KEY: Antisense oligonucleotide
        (B) LOCATION: 1...50
        (D) OTHER INFORMATION:

(xi) SEQUENCE DESCRIPTION: SEQ ID NO:9:

TGTGACCTTT TTAACATCAA CTTAATGGAG TGAGACAGTT GTCATTCGAC           50

(2) INFORMATION FOR SEQ ID NO:10:

(i) SEQUENCE CHARACTERISTICS:
        (A) LENGTH: 48 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: Hammerhead ribozyme
        (B) LOCATION: 1...48
        (D) OTHER INFORMATION:

(xi) SEQUENCE DESCRIPTION: SEQ ID NO:10:

UUCGAAACCU AUGUCAAAGC AGGNNNNCCU GAGNAGUCAG GGAGGCUU             48

(2) INFORMATION FOR SEQ ID NO:11:

(i) SEQUENCE CHARACTERISTICS:
        (A) LENGTH: 72 base pairs
        (B) TYPE: nucleic acid
        (C) STRANDEDNESS: single
        (D) TOPOLOGY: linear (ii) MOLECULE TYPE: DNA (ix) FEATURE:
        (A) NAME/KEY: Hammerhead ribozyme
        (B) LOCATION: 1...72
        (D) OTHER INFORMATION:

(xi) SEQUENCE DESCRIPTION: SEQ ID NO:11:

AAAGGGAGGC UUAACUGAGG GGUCAAAGCA GGNNNNCCUG AGNAGUCAGC GGCCUGCUGA    60

AUAGUUGAUG UC                                                       72
```